US008597549B2

(12) United States Patent
Cumpston et al.

(10) Patent No.: US 8,597,549 B2
(45) Date of Patent: Dec. 3, 2013

(54) TWO-PHOTON OR HIGHER-ORDER ABSORBING OPTICAL MATERIALS FOR GENERATION OF REACTIVE SPECIES

(75) Inventors: Brian Cumpston, Sunnyvale, CA (US); Matthew Lipson, Sunnyvale, CA (US); Seth R. Marder, Tucson, AZ (US); Joseph W. Perry, Tucson, AZ (US)

(73) Assignee: The California Institute of Technology, Pasadena, CA (US)

( * ) Notice: Subject to any disclaimer, the term of this patent is extended or adjusted under 35 U.S.C. 154(b) by 1364 days.

(21) Appl. No.: 11/768,898

(22) Filed: Jun. 26, 2007

(65) Prior Publication Data

US 2008/0283804 A1 Nov. 20, 2008

Related U.S. Application Data

(63) Continuation of application No. 10/442,431, filed on May 20, 2003, now Pat. No. 7,235,194, and a continuation of application No. 09/292,652, filed on Apr. 15, 1999, now Pat. No. 6,608,228, and a continuation-in-part of application No. 08/965,945, filed on Nov. 7, 1997, now Pat. No. 6,267,913.

(60) Provisional application No. 60/082,128, filed on Apr. 16, 1998, provisional application No. 60/029,437, filed on Nov. 12, 1996, provisional application No. 60/030,141, filed on Nov. 12, 1996.

(51) Int. Cl.
| | |
|---|---|
| *F21V 9/00* | (2006.01) |
| *G02B 5/02* | (2006.01) |
| *G02C 7/10* | (2006.01) |
| *G02F 1/361* | (2006.01) |
| *G03B 11/00* | (2006.01) |
| *G03C 1/00* | (2006.01) |
| *G03G 5/00* | (2006.01) |

(52) U.S. Cl.
USPC .............. 252/582; 252/301.35; 252/501.1; 252/583; 252/586; 252/600; 430/56; 430/72; 430/73; 564/308; 568/77

(58) Field of Classification Search
USPC .......... 252/301.17, 301.21, 301.22, 582, 583, 252/600, 586, 301.35, 501.1; 430/56, 72, 430/73; 544/296; 564/308; 568/77
See application file for complete search history.

(56) References Cited

U.S. PATENT DOCUMENTS

| | | | | |
|---|---|---|---|---|
| 5,347,040 | A * | 9/1994 | Reiser et al. | 560/139 |
| 5,446,172 | A * | 8/1995 | Crivello et al. | 549/62 |
| 5,468,890 | A * | 11/1995 | Herzig et al. | 556/12 |
| 6,267,913 | B1 * | 7/2001 | Marder et al. | 252/582 |
| 2010/0207078 | A1 * | 8/2010 | Marder et al. | 252/586 |

OTHER PUBLICATIONS

Prosecution History of U.S. Appl. No. 09/918,874, Jul. 18, 2011.
Prosecution History of U.S. Appl. No. 12/373,318, Jul. 18, 2011.

\* cited by examiner

*Primary Examiner* — Bijan Ahvazi
(74) *Attorney, Agent, or Firm* — David W. Maher; Maher Law Corp.

(57) ABSTRACT

Disclosed are highly efficient multiphoton absorbing compounds and methods of their use. The compounds generally include a bridge of pi-conjugated bonds connecting electron donating groups or electron accepting groups. The bridge may be substituted with a variety of substituents as well. Solubility, lipophilicity, absorption maxima and other characteristics of the compounds may be tailored by changing the electron donating groups or electron accepting groups, the substituents attached to or the length of the pi-conjugated bridge. Numerous photophysical and photochemical methods are enabled by converting these compounds to electronically excited states upon simultaneous absorption of at least two photons of radiation. The compounds have large two-photon or higher-order absorptivities such that upon absorption, one or more Lewis acidic species, Lewis basic species, radical species or ionic species are formed.

20 Claims, 11 Drawing Sheets

00 017  10.0kV  X1.00K  38.0μm

S7179
00  012  10.0kV   X250  120μm 00 016   10.0kV   X400   75.0μm

S7179
00  010   10.0kV   X600   50.0μm

S7179
Ag COATED ANILINE-ACRYLATE
40 031 10.0kV X450 66.7μm

TWO-PHOTON OR HIGHER-ORDER ABSORBING OPTICAL MATERIALS FOR GENERATION OF REACTIVE SPECIES

CROSS REFERENCE TO RELATED APPLICATIONS

This application claims benefit as a continuation of U.S. application Ser. No. 10/442,431, filed May 20, 2003 now U.S. Pat. No. 7,235,194, issued Jun. 26, 2007, and as a continuation of U.S. application Ser. No. 09/292,652, filed Apr. 15, 1999, now U.S. Pat. No. 6,608,228, and as a continuation-in-part of U.S. application Ser. No. 08/965,945, filed Nov. 7, 1997, now U.S. Pat. No. 6,267,913, issued Jul. 31, 2001, and claims the benefit of U.S. Provisional Application Ser. No. 60/082,128, filed Apr. 16, 1998, all of which are incorporated herein by reference in their entirety. Additionally, U.S. Pat. No. 6,267,913 claims benefit to Provisional Applications Nos. 60/029,437 and 60/030,141, both filed Nov. 12, 1996.

ORIGIN OF INVENTION

The invention described herein was made in the performance of work under a NASA contract and is subject to the provisions of Public Law 96-517 (35 U.S.C. 202) in which the Contractor has elected to retain title. The invention was also partially supported by the United States Government through the Office of Naval Research (ONR Grant Nos. N00014-95-1-1319), Air Force Office of Scientific Research (AFSOR Grant No. AFS5 F49620-97-1-0200), and the National Science Foundation (NSF Grant No. CHE 94-08701, Amendment 001).

BACKGROUND OF THE INVENTION

The invention described herein relates generally to materials which exhibit nonlinear absorptive properties as described in U.S. patent application Ser. No. 08/965,945, now U.S. Pat. No. 6,267,913, which is incorporated herein by reference. More particularly, the present invention relates to structural variants of those materials which have high two-photon or higher order absorptivities and which, due to absorption of multiple photons, undergo chemistry with high efficiency, including, but not limited to, the creation of Lewis acidic species, Lewis basic species, radical species and ionic species.

For years, the possible applications of using two-photon or higher-order absorption for a variety of applications including optical limiting, optical memory applications, microfabrication, and rational drug delivery have been considered. There are two key advantages of two-photon or higher-order induced processes relative to single-photon induced processes. 1) Whereas single-photon absorption scales linearly with the intensity of the incident radiation, two-photon absorption scales quadratically with incident intensity and higher-order absorptions will scale with yet higher powers of incident intensity. As a result, it is possible to perform multiphoton processes with three dimensional spatial resolution. 2) Because these processes involve as a first step the simultaneous absorption of two or more photons, the chromophore is excited with a number of photons whose total energy equals the energy of multi-photon absorption peak but where each photon is of insufficient energy to excite the molecule individually. Because the exciting light is not attenuated by single-photon absorption in this case, it is possible to excite molecules at a depth within a material that would not be possible via single-photon excitation by use of a beam that is focused to that depth in the material. These two advantages also apply to, for example, excitation within tissue or other biological materials. In multiphoton lithography or stereolithography, the nonlinear scaling of absorption with intensity can lead to the ability to write features below the diffraction limit of light and the ability to write features in three dimensions, which is also of interest for holography.

It was discovered in accordance with an earlier invention (as described in U.S. application Ser. No. 08/965,945, which is incorporated herein by reference) that molecules that have two or more electron donors, such as amino groups or alkoxy groups, connected to aromatic or heteroaromatic groups as part of a π-electron bridge exhibit unexpectedly and unusually high two-photon or higher-order absorptivities in comparison to, for example dyes, such as stilbene, diphenyl polyenes, phenylene vinylene oligomers and related molecules. In addition, it was found that the strength and position of the two-photon or higher-order absorption can be tuned and further enhanced by appropriate substitution of the π-electron bridge with accepting groups such as cyano. It was also discovered in accordance with the earlier invention that molecules that have two or more electron acceptors, such as formyl or dicyanomethylidene groups, connected to aromatic or heteroaromatic groups as part of a π-electron bridge exhibit unexpectedly and unusually high two-photon or higher-order absorptivities in comparison to, for example dyes, such as stilbene, diphenyl polyenes, phenylene vinylene oligomers and related molecules. The strength and position of the two-photon or higher-order absorption can likewise be tuned and further enhanced by appropriate substitution of the π-electron bridge with donating groups such as methoxy.

Realization of many of the possible applications of two-photon or higher-order absorption by dyes rests on the availability of chromophores with both large two-photon or higher-order absorption cross sections and structural motifs conducive to excited state chemical reactivity.

In 1931 Göppert-Mayer predicted molecular two-photon absorption, [Göppert-Mayer, M. *Ann. Phys.* 1931, 9, 273] and upon the invention of pulsed ruby lasers in 1960, experimental observation of two-photon absorption became reality. Multiphoton excitation has found application in biology and optical data storage, as well as in other applications. [Strickler, J. H.; Webb, W. W., *Opt. Lett.* 1991, 1780; Denk, W.; Strickler, J. H.; Webb, W. W., *Science* 1990, 248, 73; Yuste, R.; Denk, W., *Nature (London)* 1995, 375, 682; Williams, R. M.; Piston, D. W.; Webb, W. W., *FASEB J.* 1994, 8, 804; Xu, C.; Zipfel, W.; Shear, J. B.; Williams, R. M.; Webb, W. W., *Proc. Natl. Acad. Sci.* 1996, 93, 10763; Rentzepis, P. M.; Parthenopoulos, D. A., *Science,* 1989, 245, 843; Dvornikov, A. S.; Rentzepis, P. M., *Advances in Chemistry Series* 1994, 240, 161; Strickler, J. H.; Webb, W. W., *Adv. Mat.* 1993, 5, 479, U.S. Pat. Nos. 4,228,861, 4,238,840, 4,471,470, 4,333,165, 4,466,080 5,034,613 4,041,476, 4,078,229]. Although interest in multiphoton excitation has exploded, there is a paucity of two-photon absorbing dyes with adequately strong two-photon absorption in the correct spectral region for many applications. Further, there is a paucity of such chromophores that upon multiphoton excitation undergo predictable and efficient chemical reactions.

Chemistry induced by the linear absorption of electromagnetic radiation (single photon) has been proposed and exploited for polymerization initiation, photocrosslinking of polymers, holography, computer memory storage, microfabrication, medicine, and biochemistry among many other applications. Chemistry induced by linear absorption, however, allows spatial control largely limited to two dimensions (i.e., a surface). The invention described herein allows spatial control of photoinduced chemistry over three dimensions.

SUMMARY OF THE INVENTION

The present invention provides compositions of matter that have large two-photon or higher-order absorptivities and which upon two-photon or higher-order absorption lead to formation of one or more of Lewis acidic species, Lewis basic species, radical species and ionic species.

It was discovered in accordance with the present invention that chromophores that include the specific structural motifs described below allow efficient and hitherto unexplored access via multiphoton absorption to species of great material engineering, biological, and medicinal importance.

For example, compositions of the present invention are useful when incorporated into solutions, prepolymers, polymers, Langmuir-Blodgett thin films, self-assembled monolayers, and cells. The compositions can be advantageously modified to allow for variation of ease of dissolution in a variety of host media, including liquids and polymeric hosts, by changing the nature of the substituents attached to the central $\pi$-conjugated framework of the molecule as well as either the donors or acceptors, or both. In addition, by controlling the length and composition of the $\pi$-electron bridge of the molecule, it is possible to control the position and strength of the two-photon or higher-order absorption and the two-photon or higher-order excited fluorescence.

Examples of compositions in accordance with the present invention have the general formulas as shown below.

BRIEF DESCRIPTION OF THE DRAWINGS

In order to ensure a complete understanding of the present invention, the following drawings are provided in which.

DETAILED DESCRIPTION

Figure 1:
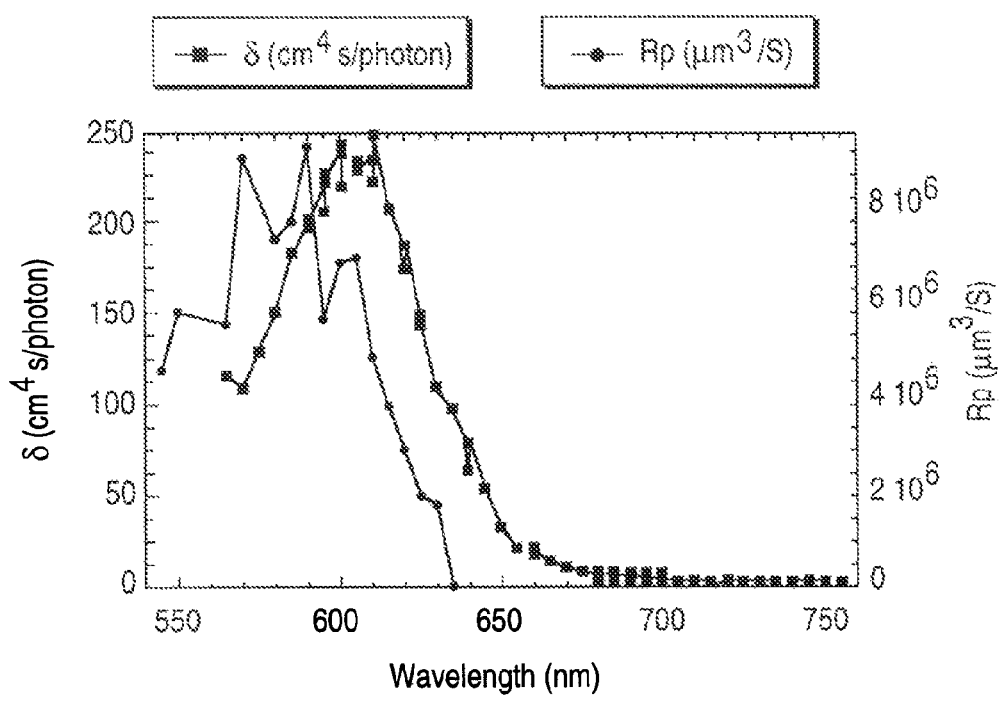
FIG. 1 is a graph showing the rate of polymerization of monomethyl-ether hydroquinone (MEHQ) inhibited Sartomer SR9008 initiated by bis-dibutylaminostilbene (BDAS) and two-photon absorptivity as a function of initiation wavelength.
Figure 2A:
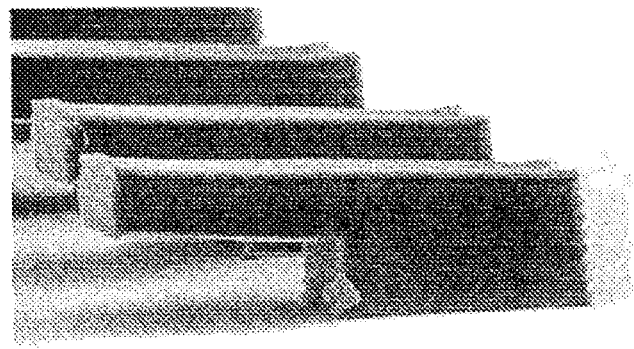
FIGS. 2*a*, *b*, *c* and *d* are SEM micrographs of cantilever and optical waveguide structures fabricated in solid films consisting of 30% w/w PSAN (75% polystyrene: 25% polyacrylonitrile copolymer), 69.9% w/w reactive monomer (50% inhibitor-free Sartomer SR9008 and 50% Sartomer SR368) and 0.1% w/w dye (1,4-bis(bis(dibutylamino)styryl) 2,5-dimethoxybenzene.
Figure 2B:
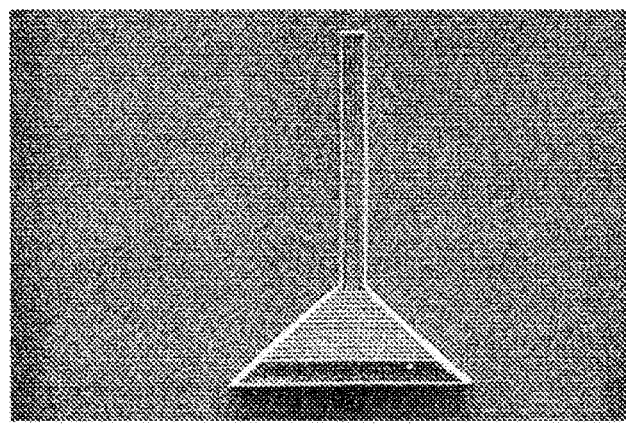
Figure 2C:
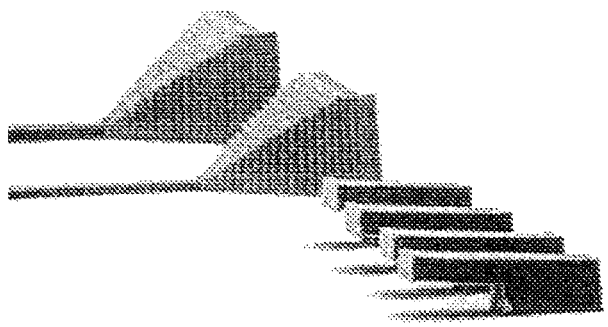
Figure 2D:
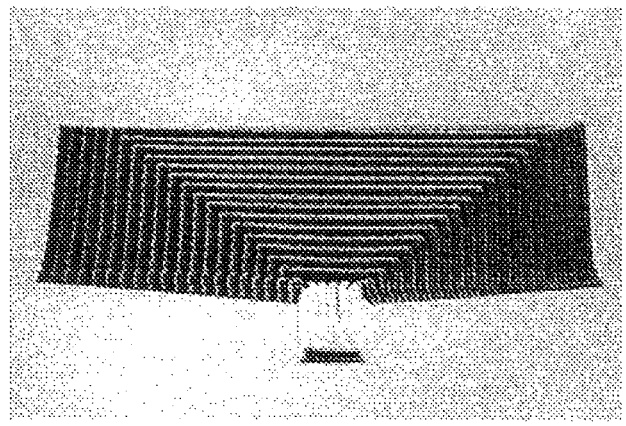

To ensure a complete understanding of the invention, the following definitions are provided:

Bridge: a molecular fragment that connects two or more chemical groups.

Donor: an atom or group of atoms with a low ionization potential that can be bonded to a $\pi$ (pi)-conjugated bridge.

Acceptor: an atom or group of atoms with a high electron affinity that can be bonded to a $\pi$ (pi)-conjugated bridge.

A more complete description of electron donors or donating groups and electron acceptors or electron accepting groups can be found in J. March, *Advanced Organic Chemistry: Reactions, Mechanisms and Structure, Fourth edition*, Wiley-Interscience, New York, 1992, Chapter 9.

Aromatic group: a carbocyclic group that contains $4n+2$ $\pi$ electrons, where n is an integer.

Heteroaromatic group: a cyclic group of atoms, with at least one atom within the ring being an element other than carbon, that contains $4n+2$ $\pi$ electrons where n is an integer.

A more complete description of aromaticity and heteroaromaticity can be found in J. March, *Advanced Organic Chemistry: Reactions, Mechanisms and Structure, Fourth edition*, Wiley-Interscience, New York, 1992, Chapter 2.

Chromophore: a molecule or aggregate of molecules that can absorb electromagnetic radiation.

Simultaneous: refers to two (or more) events that occur within the period of $10^{-14}$ sec.

Two-Photon Absorption: process wherein a molecule absorbs two quanta of electromagnetic radiation.

Multiphoton Absorption: process wherein a molecule absorbs two or more quanta of electromagnetic radiation.

Excited State: an electronic state of a molecule higher in energy than the molecule's ground state, often accessed via absorption of electromagnetic radiation and having a lifetime greater than $10^{-13}$ sec. A more complete discussion of excited states can be found in P. W. Atkins, *Physical Chemistry, Fifth edition*, W.H. Freeman, New York, 1994 and N. J Turro, *Modern Molecular Photochemistry*, Benjamin/Cumming Publishing Company, Menlo Park, 1978.

Heterolytic cleavage: fragmentation of a two-electron chemical bond such that the two electrons that composed the bond both reside on one of the two fragments formed.

Homolytic cleavage: fragmentation of a two-electron chemical bond such that each of the two fragments formed has one of the two electrons that composed the bond.

A more complete description of bond cleavage can be found in J. March, *Advanced Organic Chemistry: Reactions, Mechanisms and Structure, Fourth edition*, Wiley-Interscience, New York, 1992, page 205.

Two-photon or higher-order absorption: phenomenon wherein a molecule simultaneously absorbs two or more photons (also referred to as multi-photon absorption) without the actual population of an excited state by the absorption of a single photon.

In many cases, as will be made clear below, the molecules we teach have large two-photon or higher-order absorptivities and are themselves novel compositions of matter. The general formulas below are not inclusive of all the structures which we teach for use as two-photon or higher-order absorbers that lead to formation of Lewis acidic species, Lewis basic species, radical species, and ionic species. Other compositions which have the characteristic electronic properties as well as other advantageous properties for a variety of applications will also become apparent to those with ordinary skill in the art, when one considers the examples described in the general structures below.

U.S. application Ser. No. 08/965,945 described, in part, four structural motifs for chromophores with high two-photon or multiphoton absorptivities in which the position of two-photon or multiphoton absorption bands may be controlled. The current invention focuses on two new structural motifs that modify these chromophores such that, upon absorption of multiple photons, the chromophores will undergo chemistry with high efficiency to create one or more of Lewis acidic species, Lewis basic species, radical species, and ionic species.

Generally, the two new structural motifs of the present invention are:
(1) iodonium and sulfonium salts for use as multiphoton absorption initiated sources of Lewis acids; and
(2) fluorenyl and dibenzosuberenyl moieties for use as multiphoton absorption initiated sources of one or more of Lewis acids, Lewis bases, radical species, and ionic species.

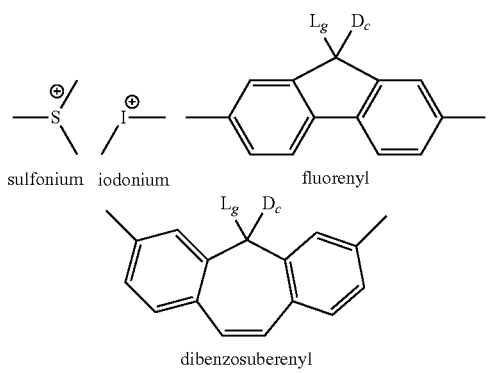

where $L_g$ (standing for a leaving group) and $D_c$ will be defined below.

The modifications used in our previous invention to tune the energetic position of the two-photon or higher-order absorption state of chromophores apply to the invention herein as well.

The advantageous inclusion of moieties of known excited state reactivity in chromophores with strong two-photon or multi-photon absorption allows the compounds described herein to have a great variety of novel and useful applications including, but not limited to
(1) two-photon generation of charge carriers, especially in photorefractive polymers;
(2) initiation of changes in host media to allow the writing of holographic information;
(3) optical lithography and three dimensional optical memory;
(4) microfabrication of three dimensional objects; and
(5) in vivo or in vitro decaging of biochemical substrates for biological, physiological, or medicinal purposes.

A more extensive listing of applications that would be rendered substantially more useful by virtue of the large two-photon or multi-photon absorptivities of the compounds described herein can be found for example in U.S. Pat. Nos. 4,228,861, 4,238,840, 4,471,470, 4,333,165, 4,466,080 and 5,034,613.

Sulfonium- and Iodonium-Containing Chromophores

Chromophores of the present invention with large two-photon and multi-photon absorptivities containing the sulfonium or the iodonium moiety will, upon two-photon or multi-photon excitation, efficiently form protic acid. Photoacid generation using compounds containing sulfonium or iodonium moieties has been documented in R. S. Davidson, "The Chemistry of Photoinitiators—Some Recent Developments", *J. Photochem. Photobiol. A: Chem.*, 73, 81-96 (1993) and M. Shirai and M. Tsunooka, "Photoacid and Photobase Generators: Chemistry and Applications to Polymeric Materials", *Prog. Polym. Sci.*, 21, 145 (1996). None of these disclosed molecules was, however, a strong two-photon absorber. In contrast, at least some of the compositions of the present invention have a structural framework having strong two-photon absorption and exhibit all of the advantageous characteristics of two-photon absorbers.

Synthesis of Sulfonium- and Iodonium-Containing Chromophores

Methods for the synthesis of sulfonium salts are well documented in J. L. Dektar and N. P. Hacker, "Photochemistry of Triarylsulfonium Salts", *J. Am. Chem. Soc.*, 112, 6004-6015 (1990), and U.S. Pat. No. 5,446,172, by Crivello, et al., and the references cited therein, each of which is incorporated herein by reference.

Methods for the synthesis of iodonium salts are well documented in C. Herzig and S. Scheiding, German Patent 4,142,327, CA 119,250,162 and C. Herzig, European Patent 4,219,376, CA 120,298,975, which are incorporated herein by reference.

Structure of Sulfonium- and Iodonium-Containing Chromophores

In the structural formulae herein, an asterisk (*) identifies the atom of attachment to a functional group and implies that the atom is missing the equivalent of one hydrogen that would normally be implied by the structure in the absence of the asterisk, "—" indicates a single bond between 2 atoms, "=" indicates a double bond between 2 atoms, and "≡" indicates a triple bond between 2 atoms.

One embodiment of the invention includes compounds with one of the four following general formulae General Structure 1-I

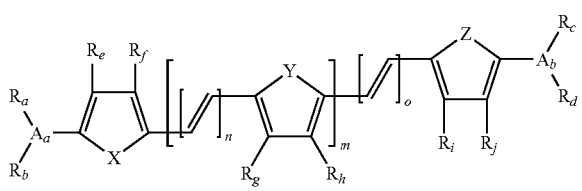

General Structure 1-II

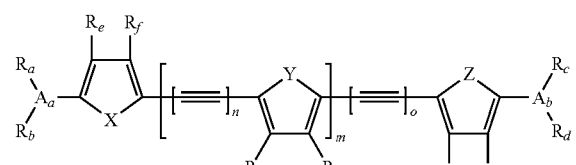

General Structure 1-III

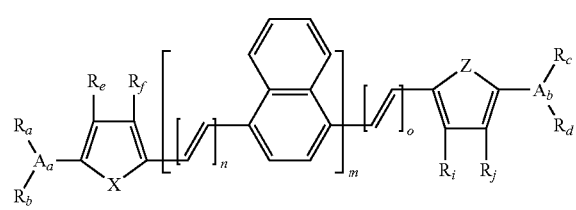

General Structure 1-IV

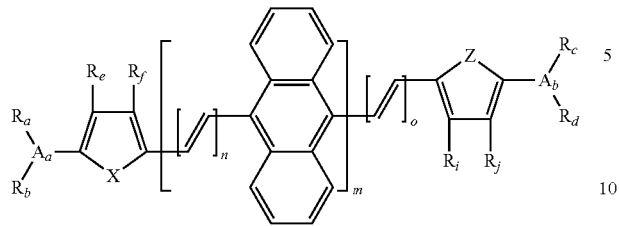

In these formulae:

$A_a$ and $A_b$
are independently selected from I$^+$ or S$^+$. To satisfy the proper bonding coordination, when $A_a$ or $A_b$ is an I$^+$ group, there is only one R group attached to the I$^+$ group; that is, $R_a$, $R_b$, $R_c$, or $R_d$ may be nothing, as required.

Anionic Counterions

All cationic species may be accompanied by counterions appropriate to make an electrically neutral complex. If, for example, the cationic species carries a double positive charge, it will be accompanied by either two singly charged anionic species or by one doubly charged anionic species. Anionic species that may be used include, but are not limited to, Cl$^-$, Br$^-$, I$^-$, and SbF$_6^-$.

m, n, and o
are integers and are independently selected such that $0 \le m \le 10$, $0 \le n \le 10$, and $0 \le o \le 10$.

X, Y, and Z
may be the same or different and may be $CR_k$=$CR_l$, O, S, or N—$R_m$; $R_k$, $R_l$, and $R_m$ are defined below.

$R_a$, $R_b$, $R_c$, and $R_d$
may be the same or different and may be
(i) H;
(ii) a linear or branched alkyl group with up to 25 carbons;
(iii) —(CH$_2$CH$_2$O)$_\alpha$—(CH$_2$)$_\beta$-Phenyl, where $0 \le \alpha \le 10$ and $1 \le \beta \le 25$;
(iv) an aryl group;
(v) a fused aromatic ring;
(vi) a polymerizable functionality; and
(vii) nothing when $A_a$ is I$^+$ or $A_b$ is I$^+$.

$R_e$, $R_f$, $R_g$, $R_h$, $R_i$, $R_j$, $R_k$, $R_l$ and $R_m$
may be the same or different and may be
(a) H;
(b) a linear or branched alkyl group with up to 25 carbons;
(c) —(CH$_2$CH$_2$O)$_\alpha$—(CH$_2$)$_\beta$OR$_{a1}$, —(CH$_2$CH$_2$O)$_\alpha$—(CH$_2$)$_\beta$NR$_{a2}$R$_{a3}$, —(CH$_2$CH$_2$O)$_\alpha$—(CH$_2$)$_\beta$CONR$_{a2}$R$_{a3}$, —(CH$_2$CH$_2$O)$_\alpha$—(CH$_2$)$_\beta$CN, —(CH$_2$CH$_2$O)$_\alpha$—(CH$_2$)$_\beta$Cl, —(CH$_2$CH$_2$O)$_\alpha$—(CH$_2$)$_\beta$Br, (CH$_2$CH$_2$O)$_\alpha$—(CH$_2$)$_\beta$I, —(CH$_2$CH$_2$O)$_\alpha$—(CH$_2$)$_\beta$-Phenyl, where $0 \le \alpha \le 10$ and $1 \le \beta \le 25$;
(d) an aryl group;
(e) a fused aromatic ring;
(f) a polymerizable functionality; or
(g) a group selected from the group consisting of —NR$_{e1}$R$_{e2}$, —OR$_{e3}$, —SR$_{e4}$, —F, —Br, —Cl, —I, and phenyl, where R$_{e1}$, R$_{e2}$, R$_{e3}$, R$_{e4}$ are independently selected from the group consisting of
(1) H;
(2) a linear or branched alkyl group with up to 25 carbons;
(3) phenyl; and
(4) a polymerizable functionality.

Aryl Group

When any of $R_a$, $R_b$, $R_c$, $R_d$, $R_e$, $R_f$, $R_g$, $R_h$, $R_i$, $R_j$, $R_k$, $R_l$ or $R_m$ is an aryl group, they may be aryl groups of the formula

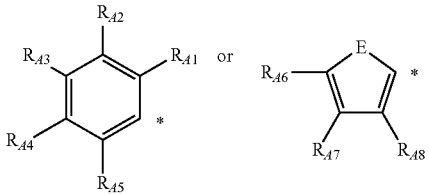

where B is —S— or —O—, and $R_{A1}$, $R_{A2}$, $R_{A3}$, $R_{A4}$, $R_{A5}$, $R_{A6}$, $R_{A7}$, and $R_{A8}$ are one of the following:
(i) H;
(ii) a linear or branched alkyl group with up to 25 carbons;
(iii) phenyl; and
(iv) —NR$_{A9}$R$_{A10}$, and —OR$_{A11}$, where R$_{A9}$, R$_{A10}$, and R$_{A11}$ are independently selected from H, a linear or branched alkyl group with up to 25 carbons, and phenyl.

Fused Aromatic Ring

When any of $R_a$, $R_b$, $R_c$, $R_d$, $R_e$, $R_f$, $R_g$, $R_h$, $R_i$, $R_j$, $R_k$, $R_l$ or $R_m$ is a fused aromatic ring, they may be

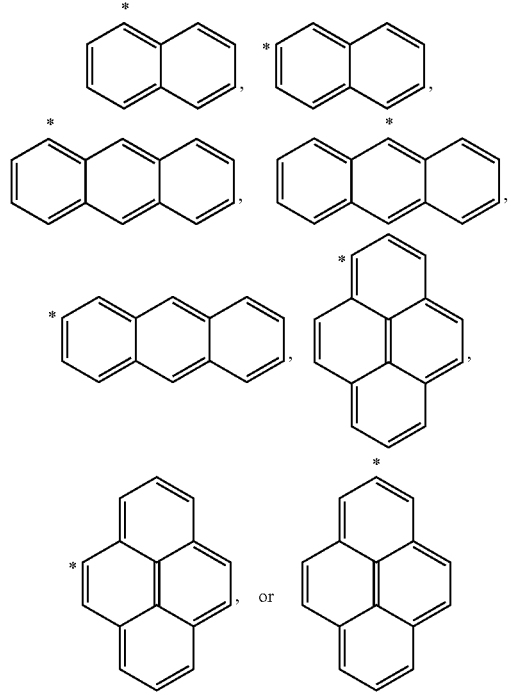

where * indicates the atom through which the fused aromatic ring is attached.

Polymerizable Functionality

When any of $R_a$, $R_b$, $R_c$, $R_d$, $R_e$, $R_f$, $R_g$, $R_h$, $R_i$, $R_j$, $R_k$, $R_l$, $R_m$, $R_{e1}$, $R_{e2}$, $R_{e3}$, or $R_{e4}$ is a polymerizable functionality, they may preferably be selected from the following:
(a) vinyl, allyl, 4-styryl, acroyl, methacroyl, epoxide (such as cyclohexene oxide), acrylonitrile, which may be polymerized by either a radical, cationic or anionic polymerization;
(b) isocyanate, isothiocyanate, epoxides such that the polymerizable functionality may be copolymerized with difunctional amines or alcohols such as HO(CH$_2$)$_\gamma$OH, H$_2$N(CH$_2$)$_\gamma$NH$_2$, where $1 \le \gamma \le 25$;

(c) strained ring olefins such as dicyclopentadienyl, norbornenyl, and cyclobutenyl where the chromophore is attached to any of the saturated carbon linkages in the strained ring olefins—in this case the monomer may be polymerized via ring opening metathesis polymerization using an appropriate metal catalyst as is known in the art; and (d) (—CH$_2$)$_\delta$SiCl$_3$, (—CH$_2$)$_\delta$Si(OCH$_2$CH$_3$)$_3$, or (—CH$_2$)$_\delta$Si(OCH$_3$)$_3$ where $0 \leq \delta \leq 25$—in this case the monomers can be reacted with water under conditions known to those skilled in the art to form either thin film or monolithic organically modified sol-gel glasses, or modified silicated surfaces.

Alkyl Groups

Unless otherwise indicated explicitly or by context, alkyl group as used in the above formulae means alkyl groups having up to 25 carbon atoms and includes both branched and straight chain alkyl groups. Exemplary alkyl groups include methyl, ethyl, propyl, butyl, pentyl, hexyl, heptyl, octyl, nonyl, in the normal, secondary, iso and neo attachment isomers.

Aryl Groups

Unless otherwise indicated explicitly or by context, aryl group as used in the above formulae means aromatic hydrocarbons having up to 20 carbon atoms. Exemplary aryl groups include phenyl, naphthyl, furanyl, thiophenyl, pyrrolyl, selenophenyl, and tellurophenyl.

Fluorenyl- and Dibenzosuberenyl-Containing Chromophores

Chromophores with large two-photon and multiphoton absorptivities containing the fluorenyl moiety will, upon two-photon or multiphoton excitation, lead to efficient homolytic and/or heterolytic cleavage, releasing the leaving group as a Lewis base, radical species, or ionic species and leaving the fluorenyl moiety as a Lewis acid, ionic species, or radical species. Appropriate choice of leaving group will tune the efficiency of cleavage and the ratio of homolytic to heterolytic cleavage. One of ordinary skill in the art will generally know how to choose the leaving group to vary the cleavage ratio as desired. Examples of previous literature addressing these issues in the context of non-multiphoton absorbing materials includes P. Wan and E. Krogh, "Contrasting Photosolvolytic Reactivities of 9-Fluorenol vs. 5-Suberenol Derivatives. Enhanced Rate of Formation of Cyclically Conjugated Four Pi Electrons Carbocations in the Excited State", *J. Am. Chem. Soc.*, 111, 4887-4895 (1989); R. A. McClelland, N, Mathivanan, and S. Steenken, "Laser Flash Photolysis of 9-Fluorenol. Production and Reactivities of the 9-Fluorenol Radical Cation and the 9-Fluorenyl Cation", *J. Am. Chem. Soc.*, 112, 4857-4861 (1990); and R. A. McClelland, F. L. Cozenes, J. Li, and S. Steenken, "Flash Photolysis Study of a Friedel-Crafts Alkylation. Reaction of the Photogenerated 9-Fluorenyl Cation with Aromatic Compounds", *J. Chem. Soc., Perkin Trans.*, 2, 1531-1543 (1996).

Further, we teach that appropriate substitution of the fluorenyl moiety and appropriate choice of environment (i.e., solvent) will tune the efficiency of cleavage and the ratio of homolytic to heterolytic cleavage, as documented in the references above and, by analogy to the behavior of the diphenylmethyl moiety, in J. Bartl, S. Steenken, M. Mayr, and R. A. McClelland, "Photo-heterolysis and Photo-homolysis of Substituted Diphenylmethyl Halides, Acetates, and Phenyl Ethers in Acetonitrile—Characterization of Diphenylmethyl Cations and Radicals Generated by 248-nm Laser Flash Photolysis", *J. Am. Chem. Soc.*, 112, 6918-6928 (1990) and M. Lipson, A. A. Deniz, and K. S. Peters, "Nature of the Potential Energy Surfaces for the $S_N1$ Reaction: A Picosecond Kinetic Study of Homolysis and Heterolysis for Diphenylmethyl Chlorides", *J. Am. Chem. Soc.*, 118, 2992-2997 (1996).

Two-photon and multiphoton absorption by the chromophores described herein containing the dibenzosuberenyl moiety will lead to efficient cleavage of the leaving group as documented in P. Wan and E. Krogh, "Contrasting Photosolvolytic Reactivities of 9-Fluorenol vs 5-Suberenol Derivatives. Enhanced Rate of Formation of Cyclically Conjugated Four Pi Electrons Carbocations in the Excited State", *J. Am. Chem. Soc.*, 111, 4887-4895 (1989); R. A. McClelland, N, Mathivanan, and S. Steenken, "Laser Flash Photolysis of 9-Fluorenol. Production and Reactivities of the 9-Fluorenol Radical Cation and the 9-Fluorenyl Cation", *J. Am. Chem. Soc.*, 112, 4857-4861 (1990); and R. A. McClelland, F. L. Cozenes, J. Li, and S. Steenken, "Flash Photolysis Study of a Friedel-Crafts Alkylation. Reaction of the Photogenerated 9-Fluorenyl Cation with Aromatic Compounds", *J. Chem. Soc., Perkin Trans.*, 2, 1531-1543 (1996).

Synthesis of Fluorenyl and Dibenzosuberenyl Containing Chromophores

Methods for the synthesis of fluorenyl and dibenzosuberenyl containing molecules are known to practitioners of the art. Exemplary synthetic procedures are given in the EXAMPLES section below.

Structure of Fluorenyl and Dibenzosuberenyl Containing Chromophores

There are two classes of compounds of the present invention containing the fluorenyl or dibenzosuberenyl groups: (1) compounds where the endgroups are electron donor groups, and (2) compounds where the endgroups are electron acceptor groups.

(1) Compounds where the Endgroups are Electron Donor Groups general structure 2-I

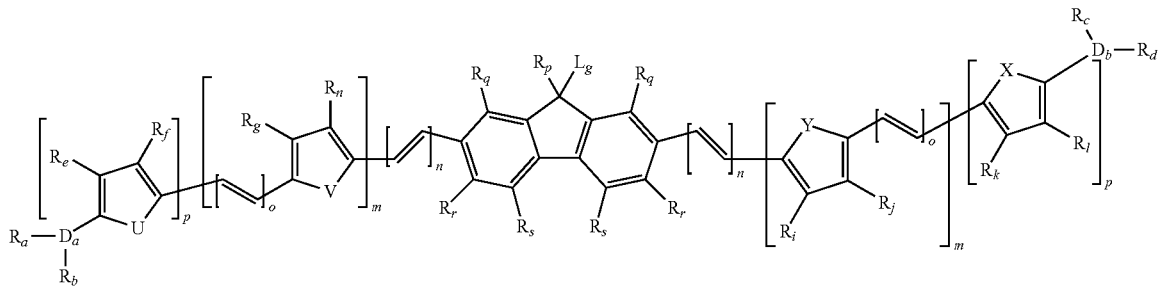

general structure 2-II

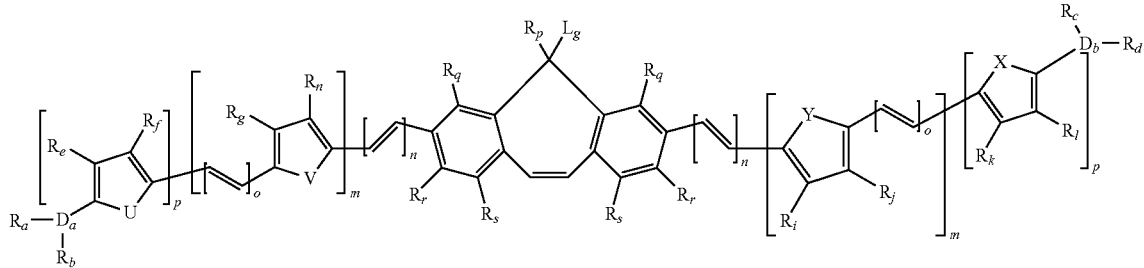

In these formulae:

$D_a$ and $D_b$
are the same or different and are N, O, S, or P. To satisfy the proper bonding coordination, when $D_a$ or $D_b$ is an —O— group or —S— group, there is only one R group attached to the $D_a$ or $D_b$ group; that is, $R_a$, $R_b$, $R_e$, or $R_d$ may be nothing, as required.

$L_g$
is a homolytic or heterolytic leaving group and may be
(i) H;
(ii) —OR$_1$, —NR$_1$R$_2$, —N$^+$R$_1$R$_2$R$_3$, —PR$_1$R$_2$, —P$^+$R$_1$R$_2$R$_3$, —SR$_1$, —S$^+$R$_1$R$_2$, Cl, Br, I, —I$^+$R$_1$, where $R_1$, $R_2$, and $R_3$ are defined below
(iii) a functional group derived essentially from an amino acids selected from the group consisting of alanine; valine; leucine; isoleucine; proline; tryptophan; phenylalanine; methionine; glycine; serine; threonine; tyrosine; cysteine; glutamine; asparagine; lysine; arginine; histidine; aspartic acid; and glutamic acid;
(iv) a polypeptide;
(v) adenine, guanine, tyrosine, cytosine, uracil, biotin, ferrocene, ruthenocene, cyanuric chloride and derivatives thereof; and
(vi) methaeryloyl chloride.

Anionic Counterions
an electrically complex neutral. If, for example, the double positive charge, it will be accompanied by either two anionic species or by one doubly charged anionic species. may be used include, but are not limited to, Cl$^-$; Br$^-$, I$^-$, and SbF$_6^-$.

m, n, o and p
are integers and are independently selected such that $0 \leq m \leq 10$, $0 \leq n \leq 10$, $0 \leq o \leq 0$, and $0 \leq \beta \leq 10$.

U, V, X, and Y
may be the same or different and may be $CR_k = CR_{1'}$, O, S, or N—$R_{m'}$; $R_{k'}$, $R_{1'}$, and $R_{m'}$ are defined below.

$R_a$, $R_b$, $R_c$, and $R_d$
may be the same or different and may be
(i) —H;
(ii) a linear or branched alkyl group with up to 25 carbons;
(iii) —(CH$_2$CH$_2$O)$_\alpha$—(CH$_2$)$_\beta$OR$_{a1}$, —(CH$_2$CH$_2$O)$_\alpha$—(CH$_2$)$_\beta$NR$_{a2}$R$_{a3}$, —(CH$_2$CH$_2$O)$_\alpha$—(CH$_2$)$_\beta$CONR$_{a2}$R$_{a3}$, —(CH$_2$CH$_2$O)$_\alpha$—(CH$_2$)$_\beta$CN, —(CH$_2$CH$_2$O)$_\alpha$—(CH$_2$)$_\beta$Cl, —(CH$_2$CH$_2$O)$_\alpha$—(CH$_2$)$_\beta$Br, —(CH$_2$CH$_2$O)$_\alpha$—(CH$_2$)$_\beta$I, —(CH$_2$CH$_2$O)$_\alpha$—(CH$_2$)$_\beta$-Phenyl, where $0 \leq \alpha \leq 10$, $1 \leq \beta \leq 25$, and where $R_{a1}$, $R_{a2}$, and $R_{a3}$, are the same or different and may be H or a linear or branched alkyl group with up to 25 carbons;
(iv) an aryl group;
(v) a fused aromatic ring;
(vi) a polymerizable functionality; and
(vii) as described above, nothing when $D_a$ or $D_b$ is an —O— group or —S— group.

$R_e$, $R_f$, $R_g$, $R_h$, $R_i$, $R_j$, $R_k$, $R_{k'}$, $R_l$, $R_{l'}$, $R_{m'}$, $R_p$, $R_q$, $R_r$, $R_s$, $R_t$, $R_u$, $R_v$ and $R_1$, $R_2$, $R_3$
may be the same or different and may be
(a) H;
(b) a linear or branched alkyl group with up to 25 carbons;
(c) —(CH$_2$CH$_2$O)$_\alpha$—(CH$_2$)$_\beta$OR$_{a1}$, —(CH$_2$CH$_2$O)$_\alpha$—(CH$_2$)$_\beta$NR$_{a2}$R$_{a3}$, —(CH$_2$CH$_2$O)$_\alpha$—(CH$_2$)$_\beta$CONR$_{a2}$R$_{a3}$, —(CH$_2$CH$_2$O)$_\alpha$—(CH$_2$)$_\beta$CN, —(CH$_2$CH$_2$O)$_\alpha$—(CH$_2$)$_\beta$Cl, —(CH$_2$CH$_2$O)$_\alpha$—(CH$_2$)$_\beta$Br, —(CH$_2$CH$_2$O)$_\alpha$—(CH$_2$)$_\beta$I, —(CH$_2$CH$_2$O)$_\alpha$—(CH$_2$)$_\beta$-Phenyl, where $0 \leq \alpha \leq 10$, $1 \leq \beta \leq 25$ and $R_{a1}$, $R_{a2}$ and $R_{a3}$ are the same or different and may be H or a linear or branched alkyl group with up to 25 carbons;
(d) an aryl group,
(e) a fused aromatic ring;
(f) a polymerizable functionality; or
(h) —NR$_{e1}$R$_{e2}$, —OR$_{e3}$, —SR$_{e4}$, —F, —Br, —Cl, —I, or phenyl, where $R_{e1}$, $R_{e2}$, $R_{e3}$, $R_{e4}$ are independently selected from the group consisting of
(1) H,
(2) a linear or branched alkyl group with up to 25 carbons;
(3) phenyl; and
(4) a polymerizable functionality.

In a preferred embodiment, $R_q$ is the same as $R_t$, $R_r$ is the same as $R_v$, and $R_s$ is the same as $R_u$.

Aryl Group
When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_{m'}$, $R_p$, $R_q$, $R_r$, $R_s$, $R_t$, $R_u$, $R_v$, $R_1$, $R_2$ or $R_3$ is an aryl group, they may be aryl groups of the formula

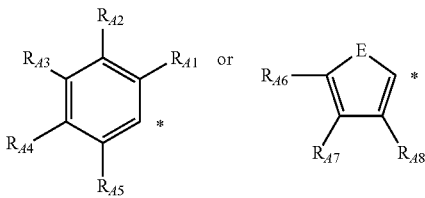

where E is —S— or —O—, and $R_{A1}$, $R_{A2}$, $R_{A3}$, $R_{A4}$, $R_{A5}$, $R_{A6}$, $R_{A7}$, and $R_{A8}$ are one of the following:
(i) H;
(ii) a linear or branched alkyl group with up to 25 carbons;
(iii) phenyl; and
(iv) —NR$_{A9}$R$_{A10}$, and —OR$_{A11}$, where $R_{A9}$, $R_{A10}$, and $R_{A11}$ are independently selected from H, a linear or branched alkyl group with up to 25 carbons, and phenyl.

Fused Aromatic Ring

When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_{m'}$, $R_p$, $R_q$, $R_r$, $R_s$, $R_t$, $R_u$, $R_v$, $R_1$, $R_2$, or $R_3$ are fused aromatic rings, they may be

[structures of naphthyl, anthracenyl isomers, and pyrenyl groups]

where * indicates the atom through which the fused aromatic ring is attached.

Polymerizable Functionality

When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_{m'}$, $R_p$, $R_q$, $R_r$, $R_s$, $R_t$, $R_u$, $R_v$, $R_1$, $R_2$, $R_3$, $R_{e1}$, $R_{e2}$, $R_{e3}$, and $R_{e4}$ is a polymerizable functionality, they may be those which can be initiated by a strong Lewis acid group such as a proton and epoxides (such as cyclohexeneoxide).

Alkyl Groups

Unless otherwise indicated explicitly or by context, alkyl group as used in the above formulae means alkyl groups having up to 25 carbon atoms and includes both branched and straight chain alkyl groups. Exemplary alkyl groups include methyl, ethyl, propyl, butyl, pentyl, hexyl, heptyl, octyl, nonyl, in the normal, secondary, iso and neo attachment isomers.

Aryl Groups

Unless otherwise indicated explicitly or by context, aryl group as used in the above formulae means aromatic hydrocarbons having up to 20 carbon atoms. Exemplary aryl groups include phenyl, naphthyl, furanyl, thiophenyl, pyrrolyl, selenophenyl, and tellurophenyl.

(2) Compounds where the Endgroups are Electron Acceptor Groups.

General Structure 3-I

[chemical structure]

General Structure 3-II

[chemical structure]

-continued

[pyrenyl structures, or]

In a preferred embodiment, $R_q$ is the same as $R_t$, $R_r$ is the same as $R_v$, and $R_s$ is the same as $R_u$.

$A_a$ and $A_b$ can be the same or different and may be —CHO, —CN, —NO$_2$, —Br, —Cl, —I or one of the following:

A1

[structure with NC, CN, and sulfone groups]

-continued
| | |
|---|---|
| 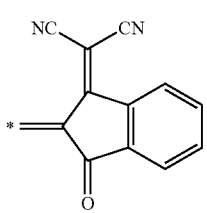 | A2 |
| 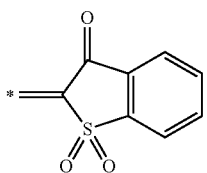 | A3 |
| 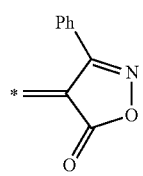 | A4 |
| 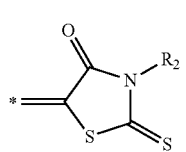 | A5 |
| 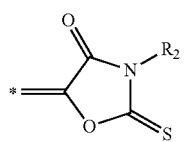 | A6 |
| 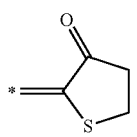 | A7 |
| 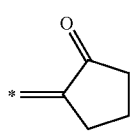 | A8 |
| 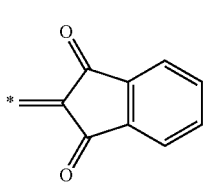 | A9 |
| 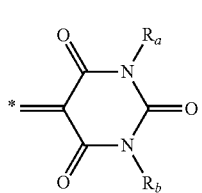 | A10 |
| 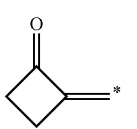 | A11 |
-continued
| | |
|---|---|
| 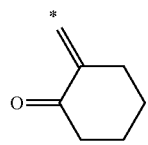 | A12 |
| 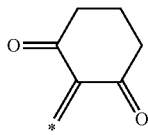 | A13 |
| 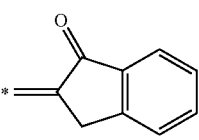 | A14 |
| 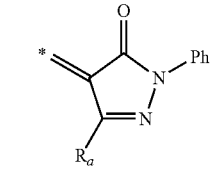 | A15 |
| 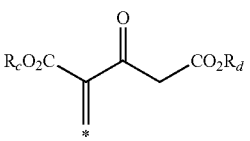 | A16 |
| 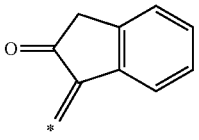 | A17 |
| 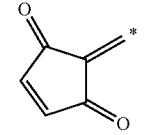 | A18 |
| 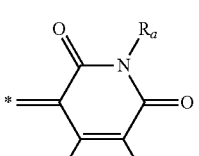 | A19 |
| 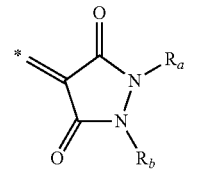 | A20 |

-continued
| | |
|---|---|
| 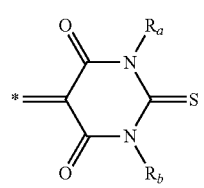 | A21 |
| 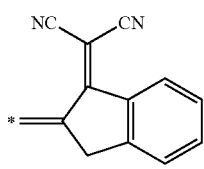 | A22 |
| 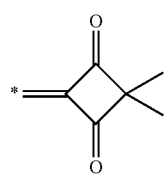 | A23 |
| 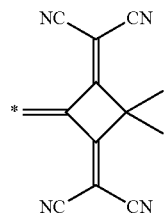 | A24 |
| 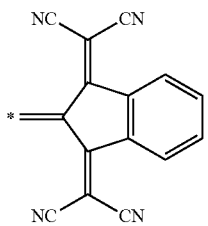 | A25 |
| 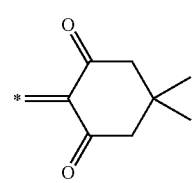 | A26 |
| 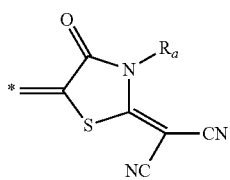 | A27 |
| 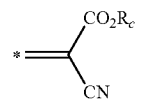 | A28 |
| 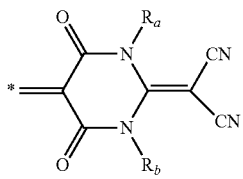 | A29 |
-continued
| | |
|---|---|
| 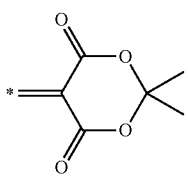 | A30 |
| | A31 |
| 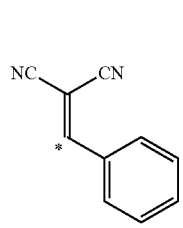 | A32 |
| 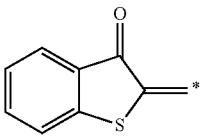 | A33 |
| | A34 |
|  | A35 |
|  | A36 |
| 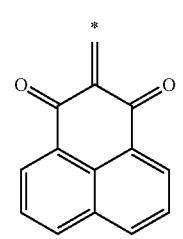 | A37 |
| 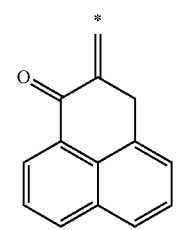 | A38 |

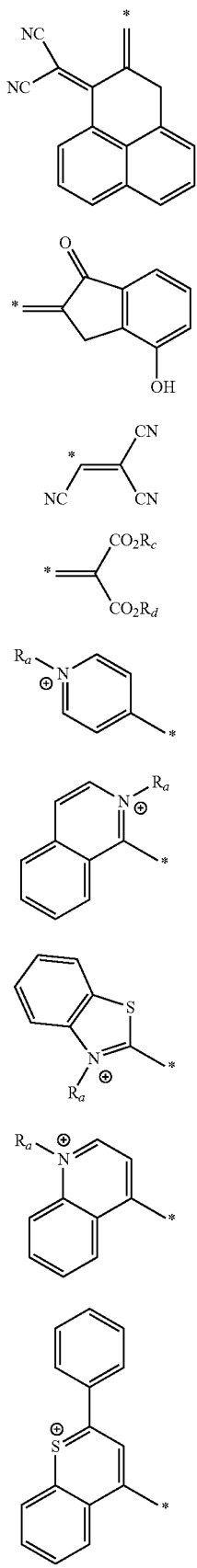

$L_g$ is a homolytic or heterolytic leaving group and may be
(i) H;
(ii) —OR$_1$, —NR$_1$R$_2$, —N$^+$R$_1$R$_2$R$_3$, —P$^+$R$_1$R$_2$, —P$^+$R$_1$R$_2$R$_3$, —SR$_1$, —S$^+$R$_1$R$_2$, Cl, Br, I, —I$^+$R$_1$, where R$_1$, R$_2$, and R$_3$ are defined below;
(iii) a functional group derived essentially from an amino acids selected from the group consisting of alanine; valine; leucine; isoleucine; proline; tryptophan; phenylalanine; methionine; glycine; serine; threonine; tyrosine; cysteine; glutamine; asparagine; lysine; arginine; histidine; aspartic acid; and glutamic acid;
(iv) a polypeptide;
(v) adenine, guanine, tyrosine, cytosine, uracil, biotin, ferrocene, ruthenocene, cyanuric chloride and derivatives thereof; and
(vi) methacryloyl chloride.

Anionic Counterions

All cationic species are accompanied by counterions appropriate to make an electrically neutral complex. If, for example, the cationic species carries a double positive charge, it will be accompanied by either two singly charged anionic species or by one doubly charged anionic species. Anionic species that may be used include, but are not limited to, Cl$^-$, Br$^-$, I$^-$, and SbF$_6^-$.

m, n, and o
are integers and are independently selected such that $0 \le m \le 10$, $0 \le n \le 10$, and $0 \le o \le 10$.

U, V, X, and Y
may be the same or different and may be CR$_k$, —CR$_l$, O, S, or N—R$_m$; R$_k$, R$_l$, and R$_m$ are defined below.

$R_a$, $R_b$, $R_c$, and $R_d$
may be the same or different and may be
(i) H;
(ii) a linear or branched alkyl group with up to 25 carbons;
(iii) —(CH$_2$CH$_2$O)$_\alpha$—(CH$_2$)$_\beta$OR$_{a1}$, —(CH$_2$CH$_2$O)$_\alpha$—(CH$_2$)$_\beta$NR$_{a2}$R$_{a3}$, —(CH$_2$CH$_2$O)$_\alpha$—(CH$_2$)$_\beta$CONR$_{a2}$R$_{a3}$, —(CH$_2$CH$_2$O)$_\alpha$—(CH$_2$)$_\beta$CN, —(CH$_2$CH$_2$O)$_\alpha$—(CH$_2$)$_\beta$Cl, —(CH$_2$CH$_2$O)$_\alpha$—(CH$_2$)$_\beta$Br, —(CH$_2$CH$_2$O)$_\alpha$—(CH$_2$)$_\beta$I, —(CH$_2$CH$_2$O)$_\alpha$—(CH$_2$)$_\beta$-Phenyl, where $0 \leq \alpha \leq 10$, $1 \leq \beta \leq 25$ and where $R_{a1}$, $R_{a2}$, and $R_{a3}$, are the same or different and may be H or a linear or branched alkyl group with up to 25 carbons;
(iv) an aryl group;
(v) a fused aromatic ring; and
(vi) a polymerizable functionality.

$R_e$, $R_f$, $R_g$, $R_h$, $R_i$, $R_j$, $R_k$, $R_{k'}$, $R_l$, $R_{l'}$, $R_m$, $R_p$, $R_q$, $R_r$, $R_s$, $R_t$, $R_u$, $R_v$, and $R_1$, $R_2$, $R_3$
may be the same or different and may be
(a) H;
(b) a linear or branched alkyl group with up to 25 carbons;
(c) —(CH$_2$CH$_2$O)$_\alpha$—(CH$_2$)$_\beta$OR$_{a1}$, —(CH$_2$CH$_2$O)$_\alpha$—(CH$_2$)$_\beta$NR$_{a2}$R$_{a3}$, —(CH$_2$CH$_2$O)$_\alpha$—(CH$_2$)$_\beta$CONR$_{a2}$R$_{a3}$, —(CH$_2$CH$_2$O)$_\alpha$—(CH$_2$)$_\beta$CN, —(CH$_2$CH$_2$O)$_\alpha$—(CH$_2$)$_\beta$Cl, —(CH$_2$CH$_2$O)$_\alpha$—(CH$_2$)$_\beta$Br, —(CH$_2$CH$_2$O)$_\alpha$—(CH$_2$)$_\beta$I, —(CH$_2$CH$_2$O)$_\alpha$—(CH$_2$)$_\beta$-Phenyl, where $1 \leq \alpha \leq 10$, $1 \leq \beta \leq 25$ and where $R_{a1}$, $R_{a2}$, and $R_{a3}$, are the same or different and may be H or a linear or branched alkyl group with up to 25 carbons;
(d) an aryl group;
(e) a fused aromatic ring;
(f) a polymerizable functionality; or
(g) —NR$_{e1}$R$_{e2}$, —OR$_{e3}$, —SR$_{e4}$, —F, —Br, —Cl, —I, or phenyl, where $R_{e1}$, $R_{e2}$, $R_{e3}$, $R_{e4}$ are independently selected from the group consisting of
(1) H;
(2) a linear or branched alkyl group with up to 25 carbons;
(3) phenyl; and
(4) a polymerizable functionality;
(5) —NR$_{e1}$R$_{e2}$, —OR$_{e3}$, —SR$_{e4}$, —F, —Br, —Cl, —I, or phenyl, Where $R_{e1}R_{e2}$, $R_{e3}$, and $R_{e4}$ may be the same or different and may be
(i) H;
(ii) a linear or branched alkyl group with up to 25 carbons;
(iii) phenyl; or
(iv) a polymerizable functionality.

Aryl Group

When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_m$, $R_p$, $R_q$, $R_r$, $R_s$, $R_t$, $R_u$, $R_v$, $R_1$, $R_2$, or $R_3$ is an aryl group, they may be aryl groups of the formula

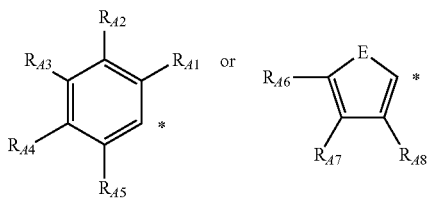

where E is —S— or —O—, and $R_{A1}$, $R_{A2}$, $R_{A3}$, $R_{A4}$, $R_{A5}$, $R_{A6}$, $R_{A7}$, and $R_{A8}$ are one of the following:
(i) H;
(ii) a linear or branched alkyl group with up to 25 carbons;
(iii) phenyl; and
(iv) —NR$_{A9}$R$_{A10}$ and —OR$_{A8}$ where $R_{A9}$, $R_{A10}$, and $R_{A11}$ are independently selected from H, a linear or branched alkyl group with up to 25 carbons, and phenyl.

Fused Aromatic Ring

When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_m$, $R_p$, $R_q$, $R_r$, $R_s$, $R_t$, $R_u$, $R_v$, $R_1$, $R_2$, or $R_3$ is a fused aromatic ring, they may be

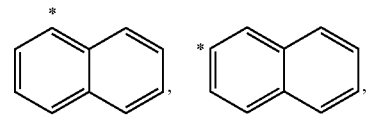

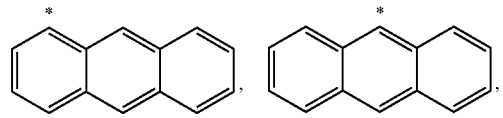

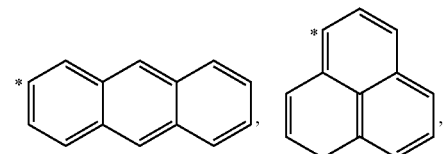

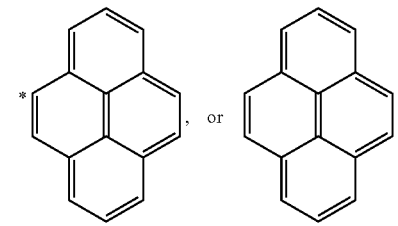

where * indicates the atom through which the fused aromatic ring is attached.

Polymerizable Functionality

When any of $R_a$, $R_b$, $R_c$, $R_d$, $R_e$, $R_f$, $R_g$, $R_h$, $R_i$, $R_j$, $R_k$, $R_{k'}$, $R_l$, $R_{l'}$, $R_m$, $R_p$, $R_q$, $R_r$, $R_s$, $R_t$, $R_u$, $R_v$, $R_1$, $R_2$, $R_3$, $R_{e1}$, $R_{e2}$, $R_{e3}$, and $R_{e4}$ are polymerizable functionalities, they may be those which can be initiated by a strong Lewis acid group such as a proton and epoxides (such as cyclohexeneoxide).

Alkyl Groups

Unless otherwise indicated explicitly or by context, alkyl group as used in the above formulae means alkyl groups having up to 25 carbon atoms and includes both branched and straight chain alkyl groups. Exemplary alkyl groups include methyl, ethyl, propyl, butyl, pentyl, hexyl, heptyl, octyl, nonyl, in the normal, secondary, iso and neo attachment isomers.

Aryl Groups

Unless otherwise indicated explicitly or by context, aryl group as used in the above formulae means aromatic hydrocarbons having up to 20 carbon atoms. Exemplary aryl groups include phenyl, naphthyl, furanyl, thiophenyl, pyrrolyl, selenophenyl, and tellurophenyl.

EXAMPLES
Examples 1-6
Exemplary Syntheses of Compounds V, VI, VIII, IX, X and XI
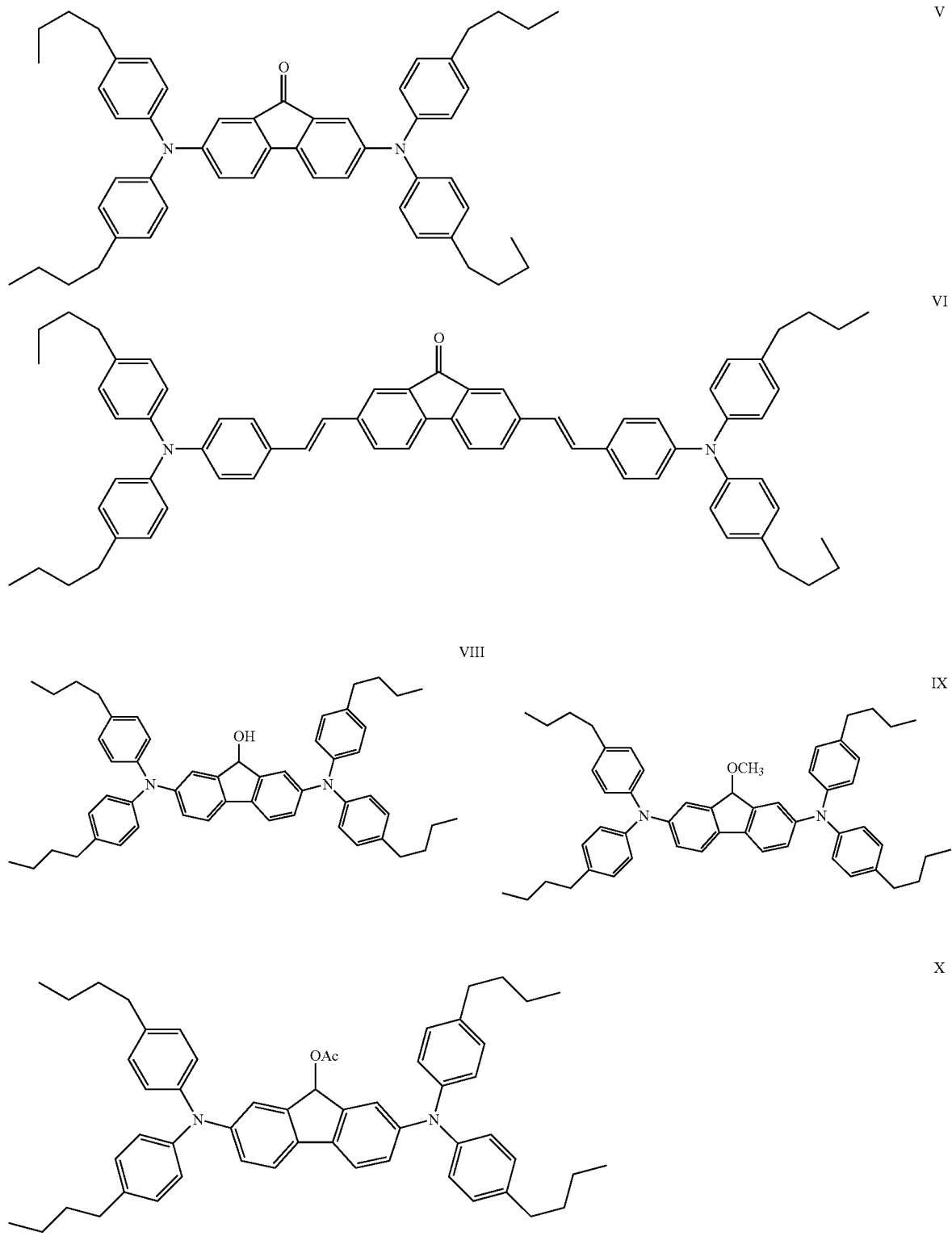

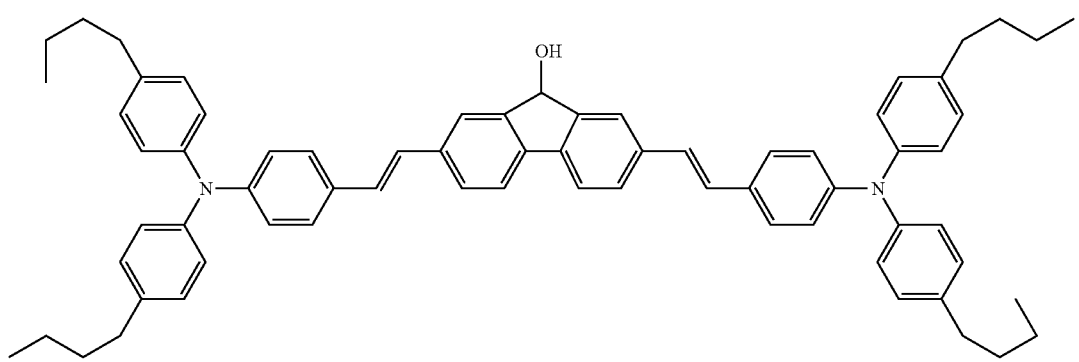

General Remarks.

$^1$H and $^{13}$C spectra were recorded on a GE QE300 spectrometer (1H at 300 MHz; $^{13}$C at 75 MHz). Mass spectral data were acquired by MALDI-TOF. Elemental (CHN) analysis were performed by Analytical Microlabs.

Example 1

Preparation of Compound V

V was synthesized via the Pd(0) catalyzed coupling of 2,7-dibromofluorenone with bis-(4n-butylphenyl)-amine under the conditions reported by Barlow and co-workers [Thayumanavan, S., Barlow, S., Marder, S. R., *Chem. Mater.*, 9, 3231-3235 (1997)] and purified by silica chromatography (10% CH$_2$Cl$_2$/hexanes). Blue oil. 43% yield. $^1$H NMR (acetone-d6, 300 MHz) δ 7.34 ppm (d, J=8.2 Hz, 2H), δ 7.13 ppm (m, 10H), δ 7.02 ppm (d, J=2.2 Hz, 2H), δ 6.98 ppm (d, J=8.4 Hz, 8H), δ 2.57 ppm (t, J=7.8 Hz, 8H), δ 1.60 ppm (m, 8H), δ 1.35 ppm (m, 8H), δ 0.92 ppm (t, J=7.3 Hz, 12H); $^{13}$C NMR (CD$_2$Cl$_2$, 75 MHz) δ 129.9 ppm (broad), δ 125.6 ppm, δ 125.4 ppm, δ125.4 ppm, δ 125.3 ppm, δ 125.2 ppm, δ 118.3 ppm, δ 35.5 ppm, δ 34.2 ppm, δ 23.0 ppm, δ 14.2 ppm. MS yields M$^+$ with m/z=738. Elemental Analysis Calculated for C$_{53}$H$_{58}$N$_2$O: C, 86.13; H, 7.91; N, 3.79. Found: C, 85.53; H, 7.97; N, 3.76.

Preparation of 2,7-dibromofluorenone 2,7-dibromofluorenone was prepared from fluorenone by the method of Dewhurst and Shah [*J. Chem. Soc. C, (Organic)* 1737-1740 (1970)] in 66% yield. 2-bromofluorenone is the major impurity and may be removed by washing the yellow solid with acetone.

Preparation of N,N-bis-(4n-butylphenyl)-amine

The preparation of bis-(4n-butylphenyl)-amine has been reported previously [Thayumanavan, S., Barlow, S., Marder, S. R., *Chem. Mater.*, 9, 3231-3235 (1997)].

Example 2

Preparation of Compound VI

VI was synthesized via the Pd(0) catalyzed Heck coupling of N,N-bis-(4-n-butylphenyl)-4-styrylamine with 2,7-dibromofluorenone in 25% yield. One equivalent of N,Nbis-(4-n-butylphenyl)-4-styrylamine was added to 0.45 equivalents 2,7-dibromofluorenone in dry dimethylformamide with 1.1 equivalents of triethylamine, 5 mole % Pd(OAc)$_2$, and 25 mole % P(o-tolyl)$_3$ and heated under argon atmosphere to 100° C. for one week. Reaction was followed by TLC and fresh catalyst and triethylamine was added every second day. Quenched reaction with water, washed into methylene chloride, and removed solvent under reduced pressure. Purified by passage through silica (1% EtOAc in hexanes as eluent). Red solid. $^1$H NMR (CD$_2$Cl$_2$, 300 MHz) δ 7.84 ppm (d, J=1.1 Hz, 2H), δ 7.61 ppm (dd, J=7.9 Hz, 1.5 Hz, 2H), δ 7.54 ppm (d, J=7.8 Hz, 2H), δ 7.42 ppm (d, J=8.8 Hz, 4H), δ7.18 ppm (d, J=16.4 Hz, 2H), δ 7.14 ppm (d, J=8.5 Hz, 8H), δ 7.0 ppm (m, 10H), δ 7.02 ppm (m, 10H), δ 2.62 ppm (t, J=7.6 Hz, 8H), δ 1.62 ppm (m, 8H), δ 1.40 ppm (m, 8H), δ 0.97 ppm (t, J=7.3 Hz, 12H); $^{13}$C NMR (CD$_2$Cl$_2$, 75 MHz) δ 193.9 ppm, δ 148.9 ppm, δ 145.6 ppm, δ 143.2 ppm, δ 139.3 ppm, δ 138.7 ppm, δ 135.6 ppm, δ 133.2 ppm, δ 130.5 ppm, δ 129.8 ppm, δ 128.0 ppm, δ 125.6 ppm, δ 125.4 ppm, δ 122.4 ppm, δ 121.6 ppm, δ 121.0 ppm, δ 35.6 ppm, δ 34.3 ppm, δ 23.0 ppm, δ 14.3 ppm. MS yields M$^+$ with m/z=942.8 Elemental Analysis Calculated for C$_{69}$H$_{70}$N$_2$O: C, 87.86; H, 7.48; N, 2.97. Found: C, 87.58; H, 7.41; N, 2.99.

Preparation of
N,N-bis-(4-n-butylphenyl)-4-styrylamine 4-(N,N-Bis-(4-n-butylphenyl)amino)benzaldehyde [Thayumanavan, S., Barlow, S., Marder, S. R., *Chem. Mater.*, 9, 3231-3235 (1997)] was stirred with 1.5 equivalents methyl triphenylphosphoniumbromide and 1.5 equivalents sodium t-butoxide in dry tetrahydrofuran under argon atmosphere overnight at RT before aqueous work-up to make the N,N-bis-(4-n-butylphenyl)-4-styrylamine. The product was purified by passage through a silica plug with hexanes and collected in 69% yield. $^1$H NMR (acetone-d6, 300 MHz) δ 7.30 ppm (d, J=8.6 Hz, 2H), δ 7.12 ppm (d, J=8.4 Hz, 4H), δ 6.96 ppm (d, J=8.4 Hz, 4H), δ 6.92 ppm (d, J=8.6 Hz, 2H), δ 6.65 ppm (dd, J=16.4 Hz, 10.9 Hz, 1H), δ 5.65 ppm (dd, J=17.6 Hz, 1.0 Hz, 1H), δ 5.10 ppm (dd, J=10.9 Hz, 0.9 Hz, 1H), δ 2.58 ppm (t, J=7.5 Hz, 4H), δ 1.58 ppm (m, 4H), δ 1.36 ppm (m, 4H), δ 0.93 ppm (t, J=7.3 Hz, 6H).

Example 3

Preparation of Compound VIII

V was reduced quantitatively to VIII with sodium borohydride in THF/ethanol at room temperature under air at RT. The course of the reaction was easily followed by the disappearance of the deep blue color of V. Light brown solid. $^1$H NMR (acetone-d6, 300 MHz) δ 7.52 ppm (d, J=8.2 Hz, 2H), δ 7.24 ppm (d, J=1.6 Hz, 2H), δ 7.14 ppm (d, J=8.6 Hz, 8H), δ 7.0 ppm (m, 10H), δ 5.43 ppm (d, J=6.7 Hz, 1H), δ 4.75 ppm (d, J=7.3 Hz, 1H), δ 2.60 ppm (t, J=7.6 Hz, 8H), δ 1.60 ppm (m, 8H), δ 1.39 ppm (m, 8H), δ 0.94 ppm (t, J=7.3 Hz, 12H).

Example 4

Preparation of Compound IX

IX was synthesized via a Williamson Ether synthesis from VIII. 1.2 equivalents of NaH were added to a deoxygenated solution of 1 equivalent of VIII and 2 equivalents of methyliodide in dry THF. Following aqueous work-up, IX was purified by silica column chromatography (0.5% EtOAc in hexanes as eluent). Brown oil, 60% yield. $^1$H NMR (acetone-d6, 300 MHz) δ 7.56 ppm (d, J=8.2 Hz, 2H), δ 7.16 ppm (m, 10H), δ 7.02 ppm (m, 10H), δ 5.39 ppm (s, 1H), δ 3.03 ppm (s, 3H), δ 2.60 ppm (t, J=7.6 Hz, 8H), δ 1.60 ppm (m, 8H), δ 1.38 ppm (m, 8H), δ 0.94 ppm (t, J=7.3 Hz, 12H).

Example 5

Preparation of Compound X

VIII was converted quantitatively to X by room temperature reaction with excess acetyl chloride in pyridine with N,N-dimethylpyridine. Solvent was removed under reduced pressure, product was taken up into hexanes, washed with water, and solvent was removed under reduced pressure. $^1$H NMR (acetone-d6, 300 MHz) δ 7.51 ppm (d, J=8.2 Hz, 2H), δ 7.20 ppm (d, J=1.9 Hz, 2H), δ 7.12 ppm (d, J=8.4 Hz, 8H), δ 6.98 ppm (m, 10H), δ 6.57 ppm (s, 1H), δ 2.58 ppm (t, J=7.7 Hz, 8H), δ 1.98 ppm (s, 3H), 1.60 ppm (m, 8H), δ 1.39 ppm (m, 8H), δ 0.93 ppm (t, J=7.3 Hz, 12H).

Example 6

Preparation of Compound XI

XI was reduced quantitatively to VI with sodium borohydride in THF/ethanol at room temperature under air at RT. The course of the reaction was easily followed by the disappearance of the red color of VI. XI may be recrystallized from hexanes. Yellow crystals. $^1$H NMR (CD$_2$Cl$_2$, 300 MHz) δ 7.84 ppm (s, 2H), δ 7.65 ppm (d, J=7.9 Hz, 2H), δ 7.54 ppm (d, J=7.9 Hz, 2H), δ 7.42 ppm (d, J=8.7 Hz, 4H), δ 7.08 ppm (m, 12H), δ 5.65 ppm (d, J=9.5 Hz, 1H), δ 2.62 ppm (t, J=7.6 Hz, 8H), δ 2.10 ppm (d, J=9.6 Hz, 1H), δ 1.61 ppm (m, 8H), δ 1.40 ppm (m, 8H), δ 0.98 ppm (t, J=7.3 Hz, 12H).

Example 7

Two-Photon Polymerization Using bis-dibutylaminostilbene (BDAS) as a Two-Photon Initiator A two-photon "polymerization action spectrum" was investigated for bis-dibutylaminostilbene (BDAS). This spectrum shows that the rate of polymerization for monomethyl-ether hydroquinone (MEHQ)-inhibited Sartomer SR9008 initiated by BDAS roughly follows the two-photon absorptivity dispersion curve, but peaks at a slightly lower wavelength.

To obtain the "action spectrum" for BDAS polymerization in SR9008, a 2.5 mM solution was used. The monomer included MEHQ inhibitor as supplied by Sartomer since the rate of initiation by BDAS is quite high. The sample was irradiated from 540 nm to 635 nm in steps of 5 nm. The sample was exposed in a square array of time along one axis and wavelength along the other. Volumes of the resulting polymer columns were measured by SEM and the rate of polymerization taken as the slope of polymer volume versus time.

A dose array experiment was performed for BDAS (#1) in MEHQ-inhibited SR9008 triacrylate monomer to investigate the wavelength dependence of the polymerization rate, $R_p$. FIG. 1 shows a plot of $R_p$ as a function of initiation wavelength. Also on this plot is the two-photon absorptivity, δ, obtained by ps (picosecond) non-linear fluorescence measurements of a 1 mM solution of BDAS in toluene. Values of $R_p$ were determined using a 2.5 mM BDAS solution in SR9008. $R_p$ is greatest at about 590 nm, 15 nm below the maximum value of δ at 605 nm. The discrepancy in wavelength may be due to linear absorption by the BDAS radical centered at 600 nm. Polymerization stopped entirely at 645 nm even though there was some two-photon absorption out to about 680 nm.

Example 8

Two-Photon Initiated Polymerization and 3D Microfabrication of Polymeric Microstructures Microfabrication was performed in solid films consisting of 30% w/w polymer binder (PSAN) (75% polystyrene:25% polyacrylonitrile copolymer), 69.9% w/w reactive monomer, and 0.1% w/w dye 1,4-bis(bis(dibutylamino)styryl) 2,5-dimethoxybenzene (compound #41). The monomer portion was 50% inhibitor-free Sartomer SR9008 (chosen for its good adhesion properties) and 50% Sartomer SR368 (an isocyanurate triacrylate, chosen for its good mechanical stability). Solutions of this composition were prepared in dioxane such that the PSAN concentration was 200 mg/ml to obtain the proper viscosity. A casting blade was used to prepare films from solution, with a wet thickness setting of 500-700 μm. Once the films dried, the thickness was about 120-180 μm. Exposure was performed using a two-photon microscope incorporating a Ti:Sapphire laser operating at 75 MHz with a pulsewidth of about 150 fs. The wavelength used was 730 nm, the two-photon absorption maximum of #41 (1,4-bis(bis(dibutyl-amino)styryl-2,5-dimethoxybenzene, and the light was focused through an oil-immersion objective with NA=1.4. X-Y-Z control of the sample was accomplished using a manipulator mounted on the microscope stage. After exposure, the unpolymerized film was washed away with dimethylformamide (DMF) and the features were characterized using SEM.

It was found that the linewidths polymerized at 730 nm (approx. 1.5 μm) were about 25% smaller than at 800 nm given the same intensity and scan rate. FIG. 2 shows cantilever and tapered waveguide structures fabricated using the procedures described above. Cantilevers with extended lengths of up to 50 μm were fabricated with no apparent sag of the unsupported arm. These cantilevers may be useful in the fabrication of optically-based chemical sensors. The waveguide structure was produced with a linespacing of 2 μm.

Example 9

Two-Photon Photodeposition of Silver Metal

In addition to using the two-photon process to initiate polymerization, it is also possible to perform metallization using this technique. Swainson provided a method for depositing Ag or $CuO_x$ using methylene blue as a sensitizer for one-photon photoreduction of a metal cation to its elemental form [W. K. Swainson and S. D. Kramer, "Method and Media for Accessing Data in Three Dimensions," U.S. Pat. No. 4,471,470 (1984)]. This process is modified for simultaneous two-photon photoreduction by use of chromophores described in this disclosure. The ability to deposit metal by a two-photon process allows fabrication of complex three-dimensional metallic or polymer/metal composite structures.

A solution of 1 g $AgNO_3$ dissolved in 10 ml DI $H_2O$ was titrated with $NH_4OH$ until the initially formed, dark precipitate was dissolved. Two drops of triethanolamine (TEA) was added to this solution along with enough chromophore, either methylene blue (MB) or lysine-substituted BDAS (LBDAS), to form a $10^{-3}$ M solution of the dye. This solution was used as prepared for solution studies or was added to an 8% by weight solution of poly(vinyl alcohol) (PVA) in DI $H_2O$ to form a castable, solid film.

Initial studies of Ag photodeposition were done using single-photon excitation in methylene blue solutions. Excitation was done at 600 nm using a 20 Hz Nd:YAG-pumped dye laser. Silver deposition was observed on the glass walls of the cell containing the silver nitrate solution. Also, a plume of silver particles could be seen in the solution, emanating from the focal point of the laser. Scanning electron microscopy (SEM) was used to examine the morphology of the deposited silver and showed that the deposited film consists of many small agglomerates. X-ray analysis confirmed that these small particles were indeed silver. Because of the roughness of these films, they are not useful for producing mirrored surfaces. The confined surface (against the glass wall of the cell), however, was a highly reflective mirror. The deposited lines were not conducting.

This technique for silver deposition from aqueous solutions was also attempted using LBDAS. This solution was pumped by two-photon excitation at 600 nm. Small amounts of Ag were deposited onto the walls of the cell and some Ag particulates were formed in solution and then settled to the bottom of the cuvette.

Initial attempts to fabricate solid or gel photopolymer films for Ag deposition were based on the aqueous silver nitrate chemistry and thus required a water soluble polymer. PVA was chosen but, because it is soluble only in boiling water, the silver salt cannot be prepared directly with the polymer solution or the reduction to Ag will occur thermally. Instead, the polymer solution was prepared and cooled and then mixed with the $AgNO_3$ solution. The combined solution was then poured into small polystyrene petri dishes and left under a halogen lamp. The photoreduction of the silver salt occurred as water evaporated from the film. The first film prepared by this method contained 17% Ag by weight. The film had good mechanical properties and was easily peeled away from the petri dish. It was dark-colored and transmitted only red light, apparently because of the size of the Ag particles in the film. The resistance of this film was 5.5 M$\Omega$. A second film was prepared with a 52% loading of Ag. This film had a shiny, metallic appearance but the film was still strong and flexible. The resistance of this film dropped to 80 k$\Omega$.

The next step was to search for a system that allows two-photon deposition of Ag. Qualitative two-photon fluorescence measurements indicated that because methylene blue had no significant two-photon absorption in the spectral region of interest, a different chromophore was needed. BDAS was chosen first and was incorporated into an aqueous solution of cellulose acetate hydroxyethyl ether and silver tetrafluoroborate ($AgBF_4$) by dissolving it in dioxane, which is completely miscible with water. In this case, $AgBF_4$ was soluble in water without the addition of $NH_4OH$ and no TEA was necessary. Upon introducing the first drop of the BDAS solution into the silver salt solution, Ag precipitated out. Table 1 shows electrochemical data for the reduction of $Ag^+$ in different solvents and free energies for electron transfer from different two-photon chromophores to $Ag^+$. It is clear that in any solvent, BDAS is such a strong reducing agent that $Ag^+$ will always be reduced thermally. The ideal situation is to use a chromophore that will not thermally reduce $Ag^+$, but will upon exposure to light. Since the HOMO-LUMO (highest occupied molecular orbital-lowest unoccupied molecular orbital) gap of BDAS and 4,4'-bis(m-tolylphenylamino)biphenyl (TPD) molecules is on the order of 3000 meV, any of these molecules will photoreduce $Ag^+$ in any solvent upon excitation.

TABLE 1

Electrochemical data for the reduction of $Ag^+$ in various solvents.

| Solvent | $E_{red.}$ $Ag^+$/Ag (mV)[a] | $\Delta G$ (meV) | | |
|---|---|---|---|---|
| | | BDAS | TPD | p-CN TPD[b] |
| $MeCl_2$ | 650 | −685 | −270 | −75 |
| DMF | 490 | −525 | −110 | 85 |
| $H_2O$ | 480 | −515 | −100 | 95 |
| Pyridine | 430 | −465 | −50 | 145 |
| THF | 410 | −445 | −30 | 165 |
| Acetone | 180 | −215 | 200 | 395 |
| $CH_3CN$ | 40 | −75 | 340 | 535 |

[a]Values of $E_{red}$ are given vs. $FcH^+$/FcH
[b]p-CN TPD = 4,4'-bis(p-cyanophenyl-m-tolylamino)biphenyl TPD was tried in an aqueous solution of $AgBF_4$ since electron transfer is only slightly downhill in this system. Although some of the TPD precipitated out of solution, it was possible to cast a film of this material. A portion of the solution that was not used was placed in sunlight and, within minutes, Ag had formed in the solution. The film was kept in the dark for several days to allow the water to evaporate. After this time, the solution was mostly clear, containing white TPD precipitates and some regions where it appears that Ag began to form. The clear portion of the film was exposed to 532 nm ns laser pulses and fairly thick deposits of Ag quickly formed in the exposed regions. Lines and patterns of Ag were deposited in this manner.

Because of the limited solubility of TPD compounds in aqueous solutions and the slow evaporation rate of water when casting films, a system based upon a non-aqueous solvent is desirable. Bis(phenyl, 4-cyanophenylamino) biphenyl (#97) was selected as the two-photon chromophore because it has one of the highest oxidation potentials of any of the two-photon chromophores that have been studied in this group (575 mV vs. $FcH^+$/FcH). Solutions of #97 and $AgBF_4$ were prepared in methylene chloride, THF, acetone, toluene, and acetonitrile and the formation of Ag was observed in all solvents except acetonitrile. This result was somewhat surprising since the value of $\Delta G$ is positive for THF (165 meV) and acetone (395 meV). The value of $\Delta G$ in acetonitrile is quite high at 535 meV. Unfortunately, it is difficult to find a polymer that is soluble in acetonitrile—at this time cellulose acetate is the only polymer found. Photopolymer films made with #97 and $AgBF_4$ in cellulose acetate/acetonitrile solutions will be studied in the near future.

Example 10

Two-Photon Excitable Photoacid Generators

The use of free-radical polymerization based on electron transfer from two-photon chromophores to acrylate monomers has proven very successful for the fabrication of microscale three-dimensional objects. Periodic structures suggestive of photonic crystals, tapered waveguide couplers, and cantilever-shaped objects have been reported in previous months. Also, high-density optical data storage based on acrylate polymerization has been demonstrated. While the size of the bits written by this method is sufficiently small to obtain storage densities of 1 terabit/cm$^3$, the speed of the recording process is too slow. Parallelization of the recording process can decrease the overall processing time, but it is also highly desirable to make the inherent response of the photopolymer material faster.

Researchers at IBM have developed chemistry for photoresist technology based on processes involving photoacid generators (PAG)—materials that produce acidic species upon exposure to light [H. Ito, "Chemical Amplification Resists: History and Development Within IBM," *IBM Journal of Research & Development*, 41, 69 (1997); R. D. Allen, G. M. Wallraff, D. C. Hofer, and R. R. Kunz, "Photoresists for 193-nm Lithography," *IBM Journal of Research & Development*, 41, 95 (1997); J. M. Shaw, J. D. Gelorme, N. C. LaBianca, W. E. Conley, and S. J. Holmes, "Negative Photoresists for Optical Lithography," *IBM Journal of Research & Development*, 41, 81 (1997)]. The driving force of this research is to develop photoresists that can be used at 193 nm, a wavelength necessary to increase the density of components in integrated circuits. The photoacid generator can initiate different chemical processes depending on the composition of the photopolymer material. For instance, the photoacid can be used to initiate cross-linking of epoxide groups. K. Y. Lee, N. LaBianca, S. A. Rishton, S. Zolghamain, J. D. Gelorme, J. Shaw, and T. H.-P. Chang, "Micromachining Applications of a High Resolution Ultrathick Photoresist," *J. Vac. Sci. Technol. B*, 13, 3012 (1995); H. Lorenz, M. Despont, N. Fahrni, N. LaBianca, P. Renaud, and P. Vettiger, "SU-8: A Low-cost Negative Resist for MEMS," *J. Micromech. Microeng.*, 121 (1997)] or it can convert aqueous-insoluble ester groups into aqueous-soluble acid groups [R. D. Allen, G. M. Wallraff, W. D. Hinsberg, and L. L. Simpson, "High Performance Acrylic Polymers for Chemically Amplified Photoresist Applications," *J. Vac. Sci. Technol. b*, 9, 3357 (1991)]. The advantage to the second process is that it can be made to be catalytic, that is, for each functional group converted, a proton is formed which can then go on to convert another group.

In this example, we extend PAG chemistry discussed above to the realm of two-photon excitation. All of the advantages of the two-photon process that have been demonstrated in acrylate polymerization can be realized. At the same time, PAG chemistry may provide a better materials system for data storage or microfabrication than acrylates. Increased sensitivity due to catalytic processes, increased mechanical stability, and decreased shrinkage upon polymerization are all possible improvements to be made. In order to realize these benefits, PAG chromophores with large two-photon absorption coefficients must be developed.

Figure 3A:
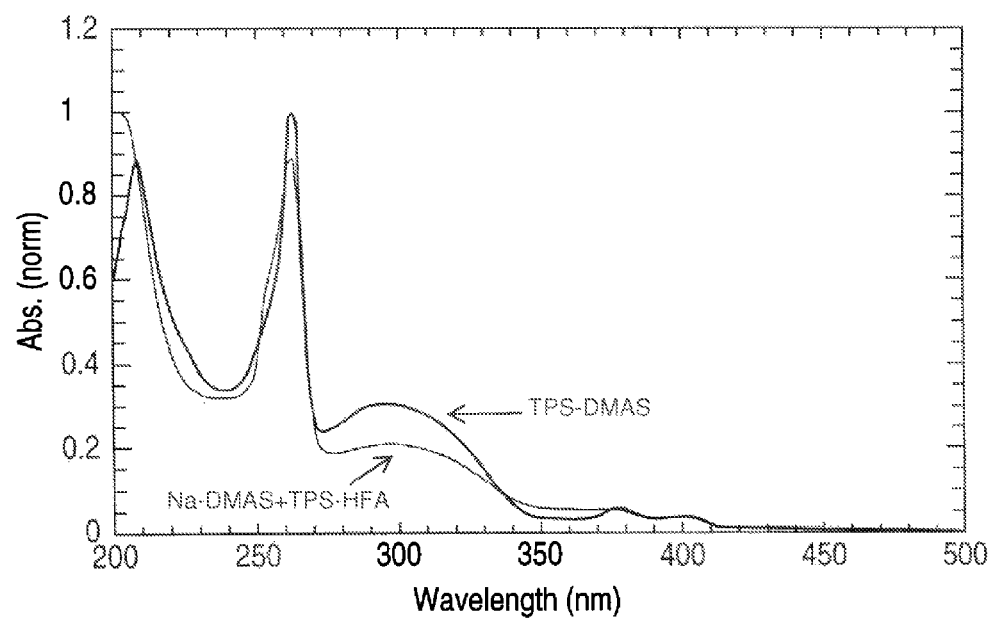
FIGS. 3*a* and 3*b* show UV-visible light absorption spectra for TPS-HFA, Na-DMAS and TPS-DMAS.
Figure 3B:
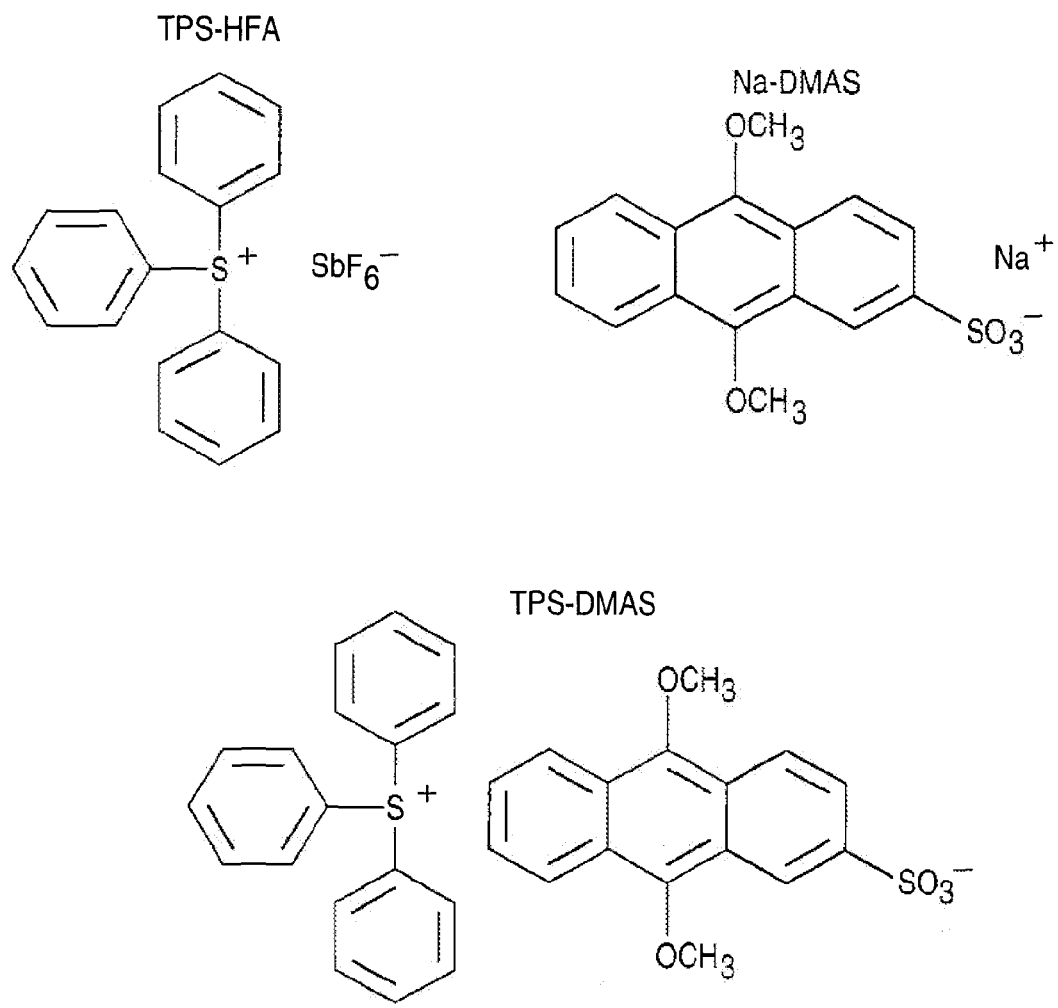

To this end, sulfonium salts with a two-photon absorbing counterion or that have significant two-photon absorption themselves are being considered. First of these is triphenylsulfonium dimethoxyanthracenesulfonate (TPS-DMAS). This material is not commercially available but has been made by anion exchange between TPS-HFA and sodium dimethoxyanthracenesulfonate (Na-DMAS) [K. Naitoh, T. Yamaoka, and A. Umehara, "Intra-ino-pair Electron Transfer Mechanism for Photolysis of Diphenyliodonium Salt Sensitized by 9,10-Dimethoxyanthracene-2-sulfonate Counteranion," *Chem. Lett.*, 1869 (1991)]. 150 mg of sodium dimethoxyanthracene sulfonate (Na-DMAS) was dissolved in 50 ml of hot DI H$_2$O. To this hot solution was added 440 µL of a 50 wt % solution of triphenylsulfonium hexafluoroantimonate (TPS-SbF$_6$ (also referred to herein as TPS-HFA)), giving equimolar amounts of the two salts. The solution was vigorously shaken and then cooled at 4° C. for about 16 hours. A waxy solid precipitated onto the walls of the flask during this time. The solid was dried overnight under vacuum. At this point, a viscous liquid was present at the bottom of the flask, presumably propylene carbonate. The precipitate was dissolved into about 4 ml acetonitrile (CH$_3$CN) and re-precipitated from 350 ml DI H$_2$O at 4° C. This solution was vacuum filtered through a fine frit, scraped and dried overnight under vacuum at 35-40° C. The yield for the entire procedure was about 75%. Solutions of all three salts were prepared in acetonitrile and their UV-Vis spectra are shown in FIG. 3a along with their structures (FIG. 3b). It is clear that the spectrum of TPS-DMAS prepared by this method has features of both Na-DMAS and TPS-HFA, as desired. Solubility properties also suggest that the salt obtained by this preparation is TPS-DMAS.

A $5 \times 10^{-4}$ M solution of TPS-DMAS was prepared in CH$_3$CN. The two-photon fluorescence signal was measured using an unamplified PMT at 700 V under excitation at 2 mJ by a ns OPO tunable laser. The fluorescence signal was collected through a 450 nm shortpass filter and a monochromator tuned to 430 nm, the fluorescence maximum of TPS-DMAS. Two-photon fluorescence excitation spectra were measured for both TPS-DMAS and Na-DMAS by scanning the OPO from 500 nm to 690 nm. Some background signal was detected from CH$_3$CN alone and was subtracted from the sample signals at each wavelength.

Figure 4:
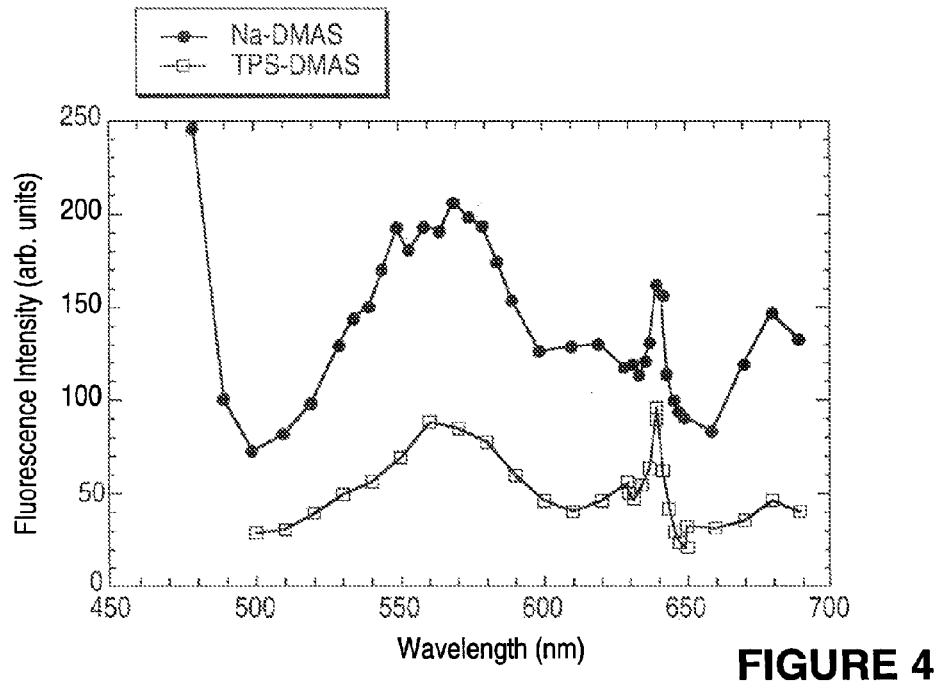
FIG. 4 shows two-photon fluorescence excitation spectra of Na-DMAS and TPS-DMAS.

FIG. 4 shows the two-photon fluorescence excitation spectra for both TPS-DMAS and Na-DMAS. Both compounds show identical features, although Na-DMAS appeared more fluorescent than TPS-DMAS. Both show a broad feature centered at about 570 nm. Also, there is a sharp feature at 645 nm which is apparently an artifact due to 400 nm light "leaking" out of the laser when excitation around 640 nm was employed.

Figure 5:
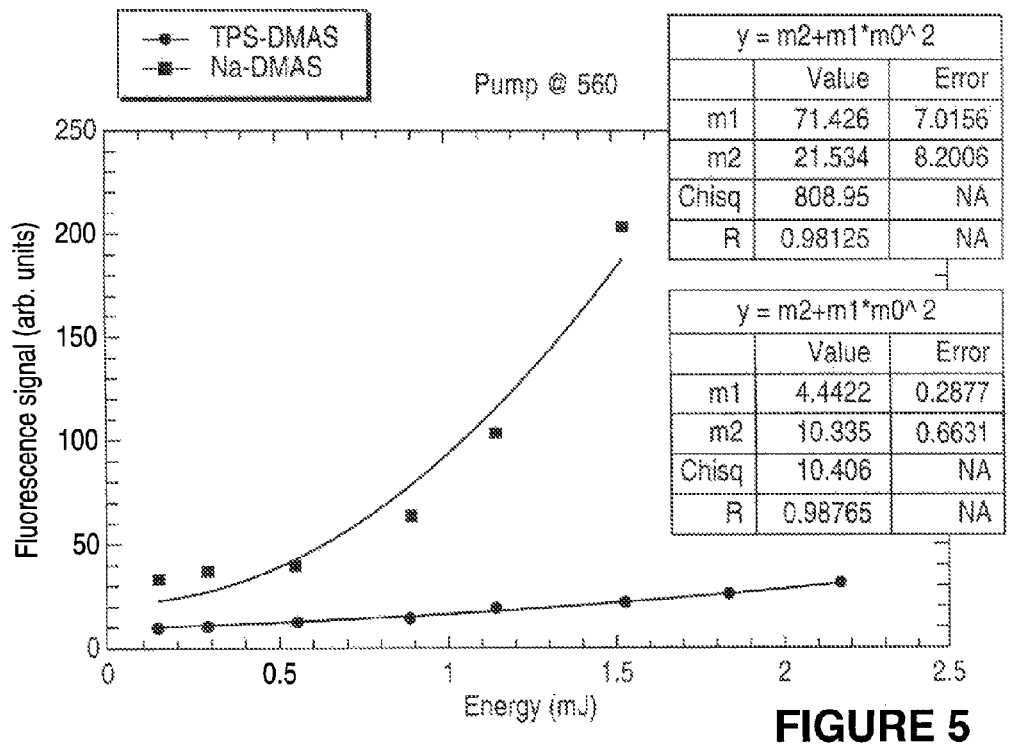
FIG. 5 shows the two-photon fluorescence spectra of Na-DMAS and TPS-DMAS as a result of "pumping" at 560 nm.

FIG. 5 shows that the fluorescence signal when pumped at 560 nm, the two-photon absorption maximum, of both compounds is proportional to the square of the excitation energy, consistent with a two-photon process. This observation also indicates that there are no saturation effects at this pump energy. We have also observed two-photon excited fluorescence of TPS-DMAS following excitation with 150 fs laser pulses at 800 nm.

These observations show that there is sufficient two-photon absorption in TPS-DMAS at 560 nm to make it a good candidate for use as a two-photon photoacid generator at this wavelength. The utility of this material in combination with multi-functional epoxide resins or as a material for selectively imparting water solubility to acrylate polymers remains to be explored.

Figure 6:
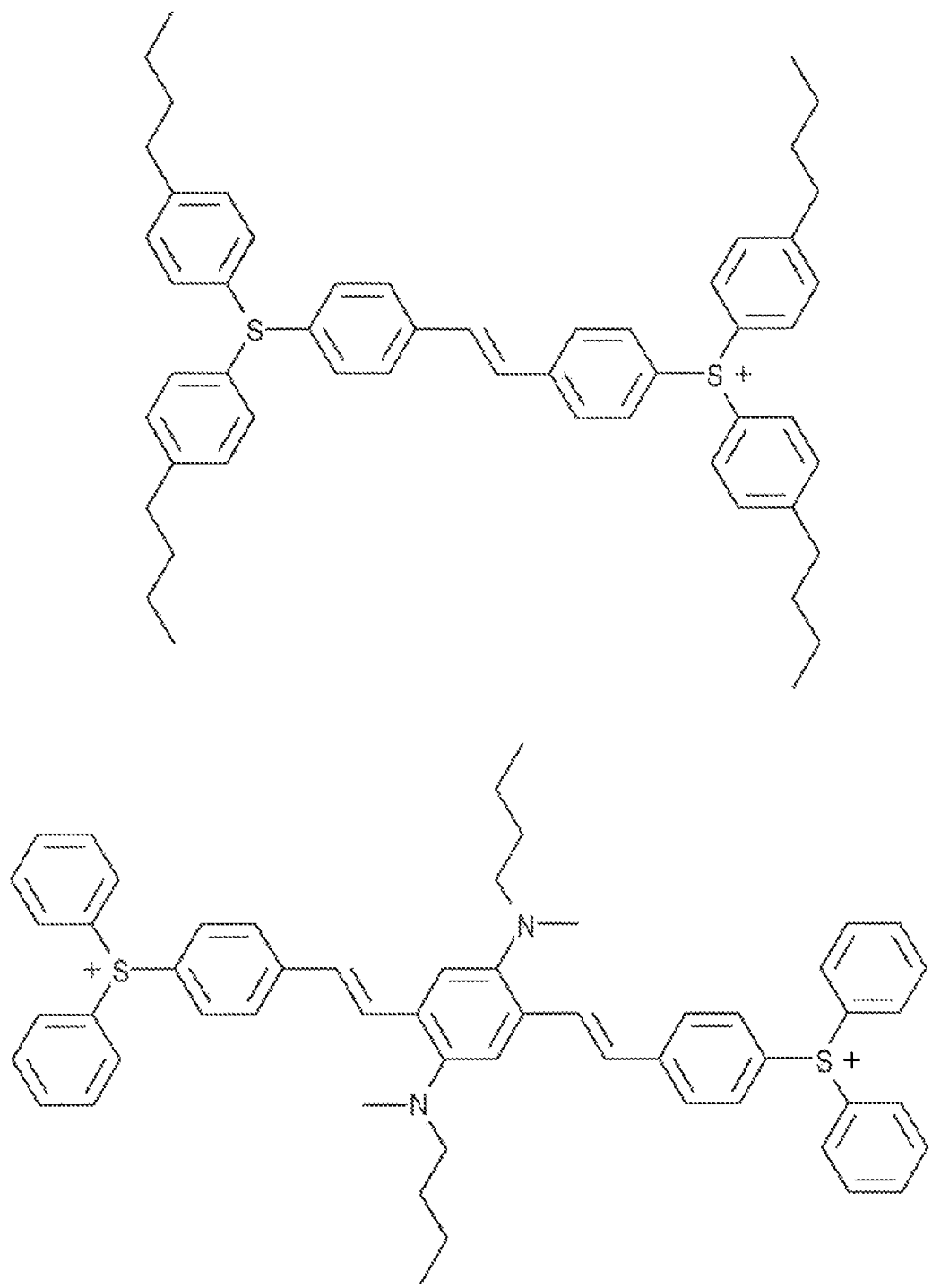
FIG. 6 illustrates the potential chemical structure of photoacid generator compounds having strong two-photon absorption according to the invention.

FIG. 6 shows potential structures of PAGs that inherently possess good two-photon absorption. These molecules actually contain two PAG groups which could provide true chemical amplification by producing two protons from a single functional group modification. Strong two-photon absorption is anticipated because the A-Π-A and A-D-A structures are analogous to D-Π-D and D-A-D molecules already shown to have high two-photon absorption cross-sections. The alkyl chains on the proposed structures are present to improve the solubility of the chromophores.

Example 11

Figure 7:
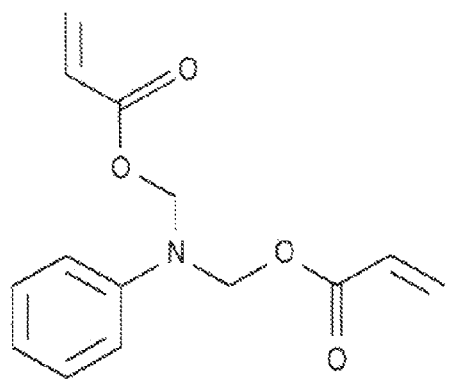
FIGS. 7 and 8 illustrate the chemical structure of aniline diacrylate (ADA), a composition according to the invention, and its absorption spectrum, respectively.

Two-Photon Polymerization of an Aniline-Substituted Diacrylate Monomer (ADA) and Subsequent Deposition of Silver Onto this Polymer ADA is a difunctional monomer. The structure of ADA is given in FIG. 7. A neat solution of aniline diacrylate (ADA) was placed in a dose array cell and polymerized using a collimated beam of ns pulses at 600 nm. Unexposed monomer was then washed away using THF. The columns were then soaked in a concentrated solution of $AgBF_4$ in $CH_3CN$ for 3 hours and analyzed using scanning electron microscopy (SEM) and energy-dispersive X-ray fluorescence spectroscopy (EDS).

A photopolymer film of ADA was prepared by dissolving 600 mg polystyrene-co-acrylonitrile (PSAN), 470 mg Sartomer SR368, 425 μL Sartomer SR9008, and 470 μL ADA in 3 ml of dioxane. This solution was cast onto a glass microscope slide using a casting knife set for a wet film thickness of 1 mm. Lines were polymerized using collimated light at 600 nm from a ns OPO laser. After polymerization, the unexposed material was removed using dimethylformamide (DMF) and the substrate was soaked for 3 hours in a concentrated solution of $AgBF_4$ in $CH_3CN$.

Figure 8:
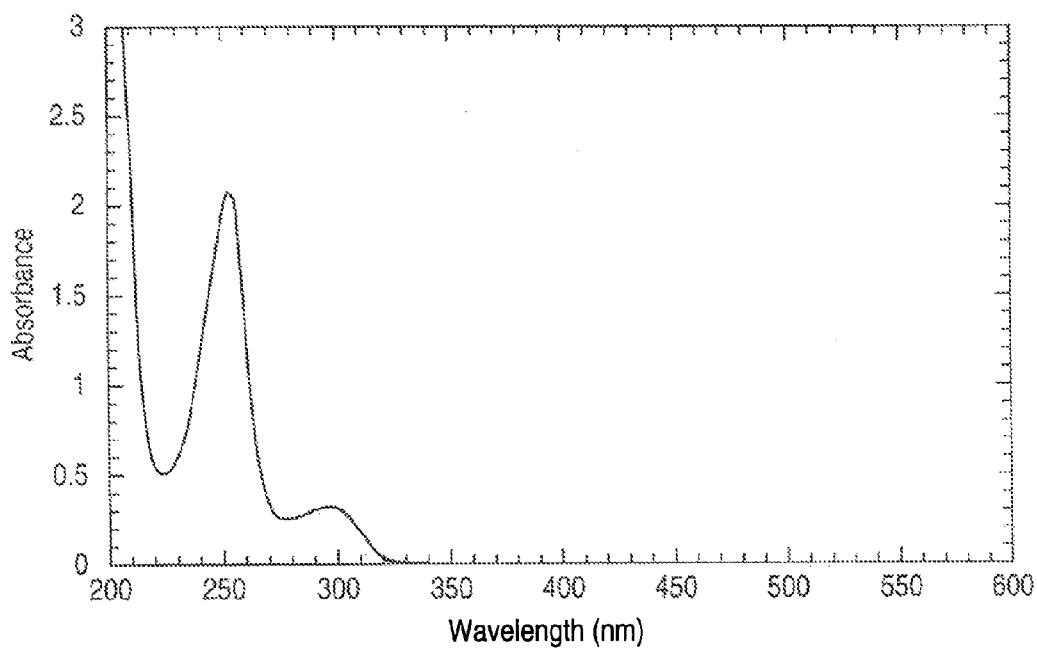

The aniline group in ADA is a sufficiently strong electron donor to thermally reduce $Ag^+$ to metallic Ag. Initial attempts to polymerize this monomer were done in a dose array fashion. It was found that polymerization occurred in neat monomer at 600 nm without the addition of any other two-photon chromophore. The absorption spectrum of ADA is given in FIG. 8 and it is clear that there is no linear absorption at 600 nm. However, the aniline absorption at 300 nm is two-photon allowed since the molecule does not have a center of symmetry. This demonstrates that the polymerization at 600 nm is due to two-photon absorption.

Figure 9:
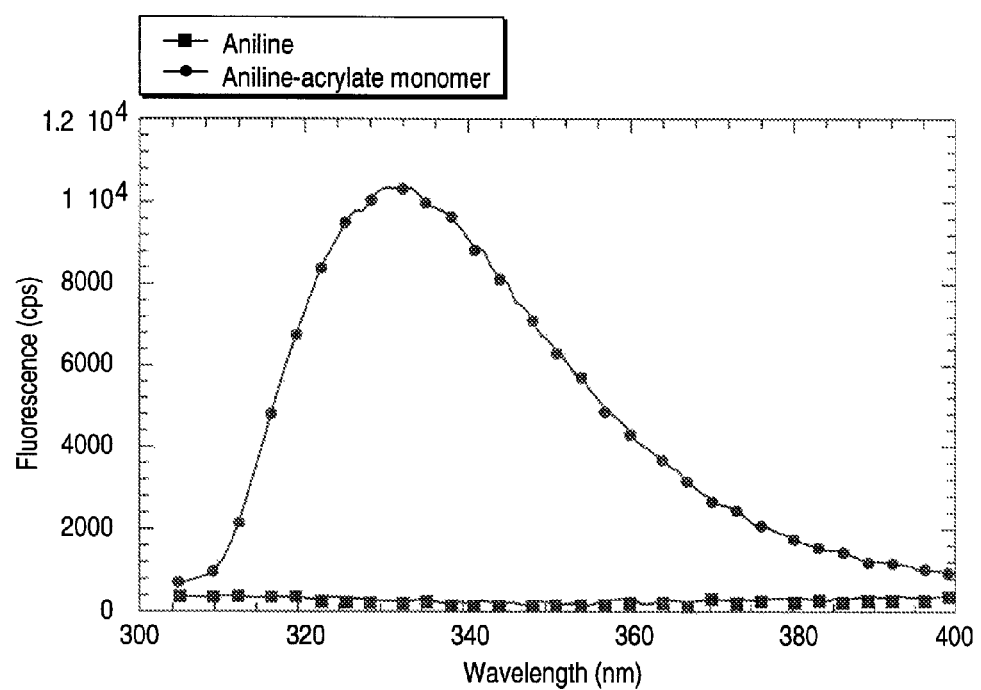
FIG. 9 shows fluorescence spectra of aniline and aniline diacrylate (ADA), after two-photon excitation at 300 nm.

Upon two-photon excitation at 600 nm, the polymerization appears to proceed by intramolecular charge transfer from the aniline group to the reactive acrylate centers. If this is the case, the fluorescence of ADA should be quenched relative to that of aniline alone. FIG. 9 shows that this is indeed the case.

Figure 10:
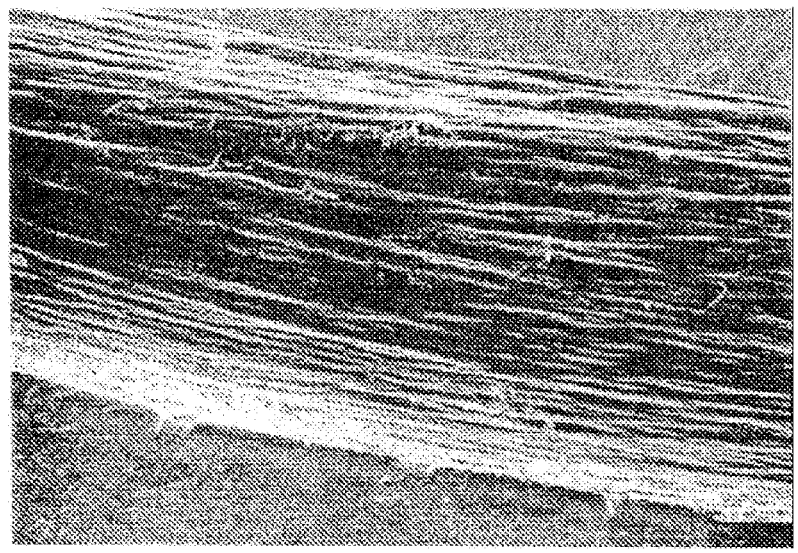
FIGS. 10 and 11 show SEM micrograph and EDS spectrum of Ag-coated poly (ADA) column.
Figure 11:
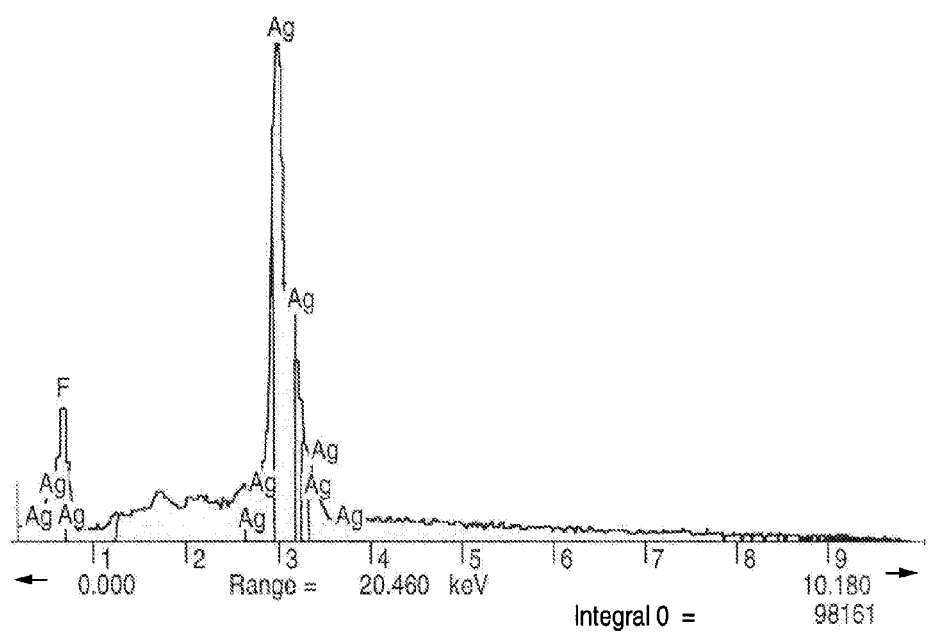

After polymerization of columns from ADA, the polymer was soaked in $AgBF_4$ to test the ability of the ADA polymer, poly(ADA), to reduce the metal cations. Indeed, the columns darkened upon exposure. SEM micrographs (FIG. 10) show that the coated polymer's morphology is consistent with previous observations in polymer columns produced by two-photon dose array experiments. X-ray fluorescence spectra (FIG. 11) indicate that the coating contains Ag and $BF_4^-$ anions. Quantitative analysis was not available by this technique.

Polymerization has also been performed in photopolymer films containing ADA. In this case, three lines were written at different energy levels and then the unexposed film was washed away. The lines remained, attached to the glass substrate. The lines darkened upon exposure to $AgBF_4$ solution, but no analysis of the coating has been performed yet.

We claim:

1. A compound selected from the group consisting of

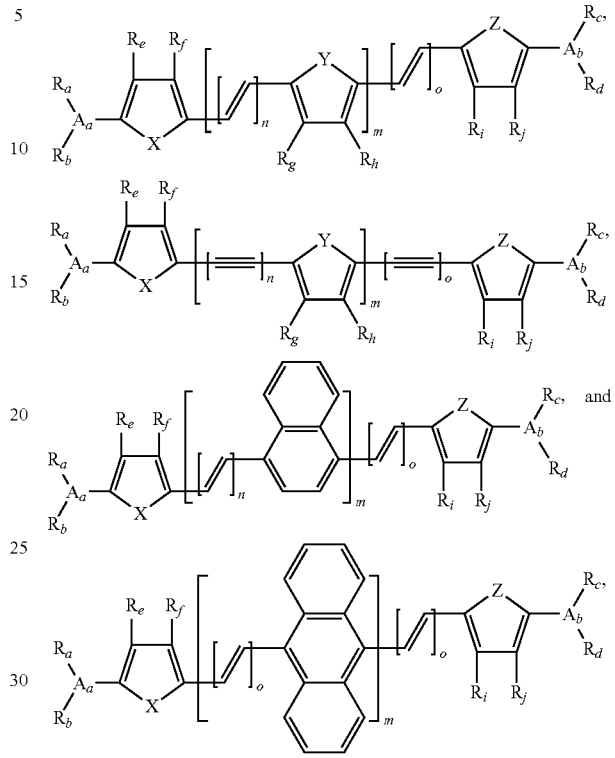

where
Aa and Ab are independently selected from the group consisting of $S^+$ and $I^+$;
m, n, o are independently selected from the range of integers greater than or equal to zero and less than or equal to ten, wherein m and/or o are at least 1;
X, Y, Z are independently selected from the group consisting of $CR_k=CR_l$, O, S, and $N-R_m$,
where $R_k$, $R_l$, and $R_m$ are defined below;
$R_a$, $R_b$, $R_c$, $R_d$ are independently selected from the group consisting of
 (i) H;
 (ii) a linear or branched alkyl group with up to 25 carbons;
 (iii) $(CH_2CH_2O)_\alpha-(CH_2)_\beta$-Phenyl, where $0 \leq \alpha \leq 10$ and $1 \leq \beta \leq 25$;
 (iv) an aryl group;
 (v) a fused aromatic ring;
 (vi) a polymerizable functionality; and
 (vii) wherein one of $R_a$ and $R_b$ is not present when $A_a$ is $I^+$, and one of $R_c$ and $R_d$ is not present when $A_b$ is $I^+$; and
$R_e$, $R_f$, $R_g$, $R_h$, $R_i$, $R_j$, $R_k$, $R_l$ and $R_m$ are independently selected from the group consisting of
 (a) H;
 (b) a linear or branched alkyl group with up to 25 carbons;
 (c) $-(CH_2CH_2O)_\alpha-(CH_2)_\beta OR_{a1}$, $-(CH_2CH_2O)_\alpha-(CH_2)_\beta NR_{a2}R_{a3}$, $-(CH_2CH_2O)_\alpha-(CH_2)_\beta CONR_{a2}R_{a3}$, $-(CH_2CH_2O)_\alpha(CH_2)_\beta CN$, $-(CH_2CH_2O)_\alpha-(CH_2)_\beta Cl$, $-(CH_2CH_2O)_\alpha-(CH_2)_\beta Br$, $-(CH_2CH_2O)_\alpha-(CH_2)_\beta I$, $-(CH_2CH_2O)_\alpha-(CH_2)_\beta$-Phenyl, where $0 \leq \alpha \leq 10$ and $1 \leq \beta \leq 25$;
 (d) an aryl group;
 (e) a fused aromatic ring;
 (f) a polymerizable functionality; and (g) a group selected from the group consisting of —NR$_{e1}$R$_{e2}$, —OR$_{e3}$, —SR$_{e4}$, —F, —Br, —Cl, —I, and phenyl, where R$_{e1}$, R$_{e2}$, R$_{e3}$, R$_{e4}$ are independently selected from the group consisting of (1) H;

(2) a linear or branched alkyl group with up to 25 carbons;

(3) phenyl; and (4) a polymerizable functionality.

2. A compound according to claim 1, further comprising an anion selected from the group consisting of Cl$^-$, Br$^-$, I$^-$, and SbF$_6^-$.

3. A compound according to claim 1, wherein the R$_a$, R$_b$, R$_c$, R$_d$, R$_e$, R$_f$, R$_g$, R$_h$, R$_i$, R$_j$, R$_k$, R$_l$, R$_m$, R$_{e1}$, R$_{e2}$, R$_{e3}$, or R$_{e4}$ polymerizable functionalities are selected from the group consisting of vinyl, allyl, 4-styryl, acroyl, methacroyl, epoxides, acrylonitrile, isocyanate, isothiocyanate, strained ring olefins, (—CH$_2$)$_\delta$SiCl$_3$, (—CH$_2$)$_\delta$Si(OCH$_2$CH$_3$)$_3$, and (—CH$_2$)$_\delta$Si(OCH$_3$)$_3$ where $0<\delta<25$.

4. A compound according to claim 3, wherein the polymerizable functionality strained ring olefins are selected from the group consisting of dicyclopentadienyl, norbornenyl, and cyclobutenyl.

5. A compound according to claim 1, wherein the R$_a$, R$_b$, R$_c$, R$_d$, R$_e$, R$_f$, R$_g$, R$_h$, R$_i$, R$_j$, R$_k$, R$_l$, R$_m$, R$_{e1}$, R$_{e2}$, R$_{e3}$, or R$_{e4}$ linear or branched alkyl groups are selected from the group consisting of methyl, ethyl, propyl, butyl, pentyl, hexyl, heptyl, octyl, nonyl, in the normal, secondary, iso and neo attachment isomers.

6. A compound according to claim 1, wherein the R$_a$, R$_b$, R$_c$, R$_d$, R$_e$, R$_f$, R$_g$, R$_h$, R$_i$, R$_j$, R$_k$, R$_l$, or R$_m$ aryl group is selected from the group consisting of

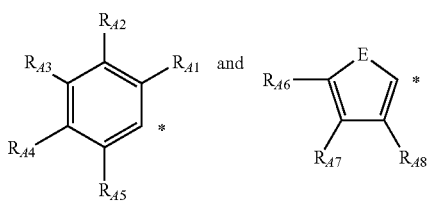

where

E is selected from the group consisting of —S— and —O—, and

R$_{A1}$, R$_{A2}$, R$_{A3}$, R$_{A4}$, R$_{A5}$, R$_{A6}$, R$_{A7}$, and R$_{A8}$ are selected from the group consisting of (i) H;

(ii) a linear or branched alkyl group with up to 25 carbons;

(iii) phenyl; and (iv) —NR$_{49}$R$_{410}$, and —OR$_{411}$, where R$_{49}$, R$_{410}$, and R$_{411}$ are independently selected from the group consisting of —H, a linear or branched alkyl group with up to 25 carbons, and phenyl.

7. A compound according to claim 6, wherein the aryl groups are selected from the group consisting of phenyl, naphthyl, furanyl, thiophenyl, pyrrolyl, selenophenyl and tellurophenyl.

8. A compound according to claim 1, wherein the R$_a$, R$_b$, R$_c$, R$_d$, R$_e$, R$_f$, R$_g$, R$_h$, R$_i$, R$_j$, R$_k$, R$_l$, or R$_m$ fused aromatic ring is selected from the group consisting of

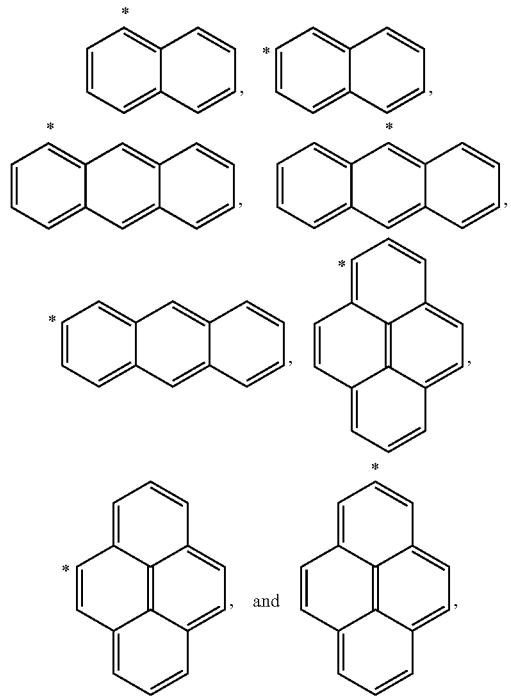

where * indicates the atom through which the fused aromatic ring is attached.

9. A photoactivated compound, wherein the compound is activated via multiphoton absorption, said compound selected from the group consisting of

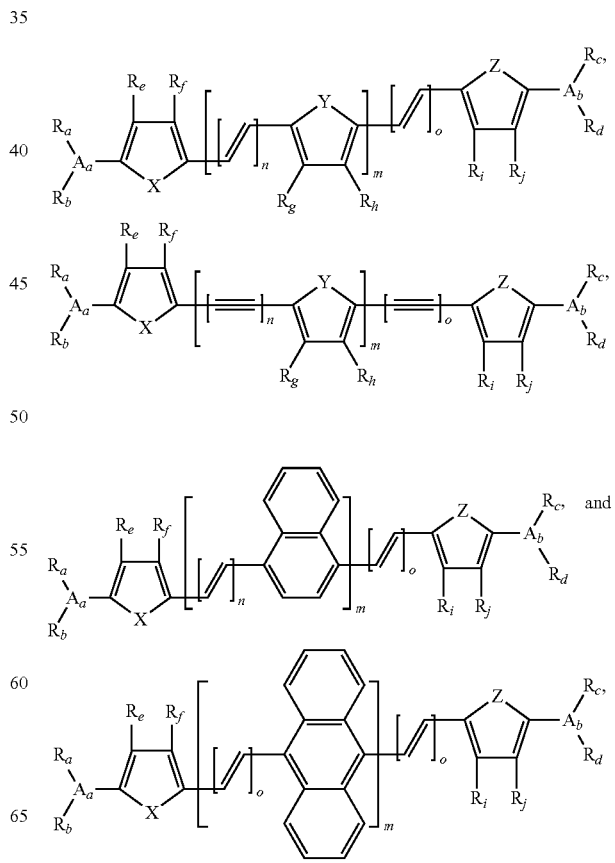

where
Aa and Ab are independently selected from the group consisting of $S^+$ and $I^+$;
m, n, o are independently selected from the range of integers greater than or equal to zero and less than or equal to ten, wherein m and/or o are at least 1;
X, Y, Z are independently selected from the group consisting of $CR_k=CR_l$, O, S, and $N-R_m$,
where $R_k$, $R_l$, and $R_m$ are defined below;
$R_a$, $R_b$, $R_c$, $R_d$ are independently selected from the group consisting of
(i) H;
(ii) a linear or branched alkyl group with up to 25 carbons;
(iii) $(CH_2CH_2O)_\alpha-(CH_2)_\beta$-Phenyl, where $0 \leq \alpha \leq 10$ and $1 \leq \beta \leq 25$;
(iv) an aryl group;
(v) a fused aromatic ring;
(vi) a polymerizable functionality; and
(vii) wherein one of $R_a$ and $R_b$ is not present when $A_a$ is $I^+$, and one of $R_c$ and $R_d$ is not present when $A_b$ is $I^+$; and
$R_e$, $R_f$, $R_g$, $R_h$, $R_i$, $R_j$, $R_k$, $R_l$ and $R_m$ are independently selected from the group consisting of
(a) H;
(b) a linear or branched alkyl group with up to 25 carbons;
(c) $-(CH_2CH_2O)_\alpha-(CH_2)_\beta OR_{a1}$, $-(CH_2CH_2O)_\alpha-(CH_2)_\beta NR_{a2}R_{a3}$, $-(CH_2CH_2O)_\alpha-(CH_2)_\beta CONR_{a2}R_{a3}$, $-(CH_2CH_2O)_\alpha(CH_2)_\beta CN$, $-(CH_2CH_2O)_\alpha-(CH_2)_\beta Cl$, $-(CH_2CH_2O)_\alpha-(CH_2)_\beta Br$, $-(CH_2CH_2O)_\alpha-(CH_2)_\beta I$, $-(CH_2CH_2O)_\alpha-(CH_2)_\beta$-Phenyl, where $0 \leq \alpha \leq 10$ and $1 \leq \beta \leq 25$;
(d) an aryl group;
(e) a fused aromatic ring;
(f) a polymerizable functionality; and
(g) a group selected from the group consisting of $-NR_{e1}R_{e2}$, $-OR_{e3}$, $-SR_{e4}$, $-F$, $-Br$, $-Cl$, $-I$, and phenyl, where $R_{e1}$, $R_{e2}$, $R_{e3}$, $R_{e4}$ are independently selected from the group consisting of
(1) H;
(2) a linear or branched alkyl group with up to 25 carbons;
(3) phenyl; and
(4) a polymerizable functionality.

10. A compound according to claim 9, further comprising an anion selected from the group consisting of $Cl^-$, $Br^-$, $I^-$, and $SbF_6^-$.

11. A compound according to claim 9, wherein the $R_a$, $R_b$, $R_c$, $R_d$, $R_e$, $R_f$, $R_g$, $R_h$, $R_i$, $R_j$, $R_k$, $R_l$, $R_m$, $R_{e1}$, $R_{e2}$, $R_{e3}$, or $R_{e4}$ polymerizable functionalities are selected from the group consisting of vinyl, allyl, 4-styryl, acroyl, methacroyl, epoxides, acrylonitrile, isocyanate, isothiocyanate, strained ring olefins, $(-CH_2)_\delta SiCl_3$, $(-CH_2)_\delta Si(OCH_2CH_3)_3$, and $(-CH_2)_\delta Si(OCH_3)_3$ where $0 < \delta < 25$.

12. A compound according to claim 11, wherein the polymerizable functionality strained ring olefins are selected from the group consisting of dicyclopentadienyl, norbornenyl, and cyclobutenyl.

13. A compound according to claim 9, wherein the $R_a$, $R_b$, $R_c$, $R_d$, $R_e$, $R_f$, $R_g$, $R_h$, $R_i$, $R_j$, $R_k$, $R_l$, $R_m$, $R_{e1}$, $R_{e2}$, $R_{e3}$, or $R_{e4}$ linear or branched alkyl groups are selected from the group consisting of methyl, ethyl, propyl, butyl, pentyl, hexyl, heptyl, octyl, nonyl, in the normal, secondary, iso and neo attachment isomers.

14. A compound according to claim 9, wherein the $R_a$, $R_b$, $R_c$, $R_d$, $R_e$, $R_f$, $R_g$, $R_h$, $R_i$, $R_j$, $R_k$, $R_l$, or $R_m$ aryl group is selected from the group consisting of

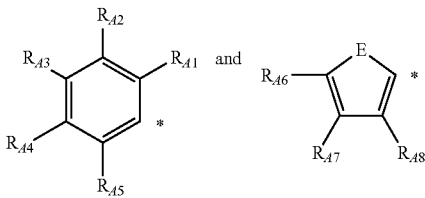

where
E is selected from the group consisting of $-S-$ and $-O-$, and
$R_{A1}$, $R_{A2}$, $R_{A3}$, $R_{A4}$, $R_{A5}$, $R_{A6}$, $R_{A7}$, and $R_{A8}$ are selected from the group consisting of
(i) H;
(ii) a linear or branched alkyl group with up to 25 carbons;
(iii) phenyl; and
(iv) $-NR_{A9}R_{A10}$, and $-OR_{A11}$, where $R_{A9}$, $R_{A10}$, and $R_{A11}$ are independently selected from the group consisting of $-H$, a linear or branched alkyl group with up to 25 carbons, and phenyl.

15. A compound according to claim 14, wherein the aryl groups are selected from the group consisting of phenyl, naphthyl, furanyl, thiophenyl, pyrrolyl, selenophenyl and tellurophenyl.

16. A compound according to claim 9, wherein the $R_a$, $R_b$, $R_c$, $R_d$, $R_e$, $R_f$, $R_g$, $R_h$, $R_i$, $R_j$, $R_k$, $R_l$, or $R_m$ fused aromatic ring is selected from the group consisting of

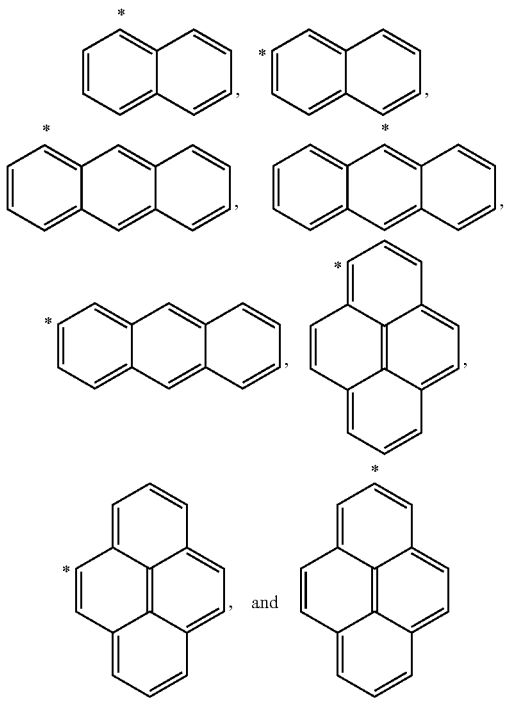

where * indicates the atom through which the fused aromatic ring is attached.

17. The compound of claim 9, wherein the compound has the formula
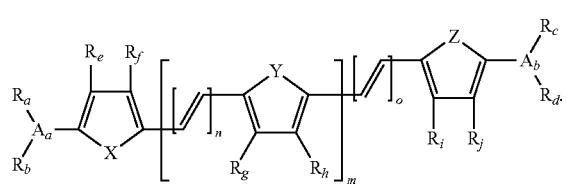
18. The compound of claim 9, wherein the compound has the formula
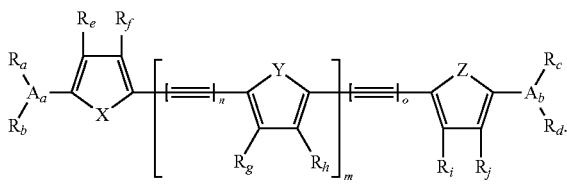
19. The compound of claim 9, wherein the compound has the formula
20. The compound of claim 9, wherein the compound has the formula
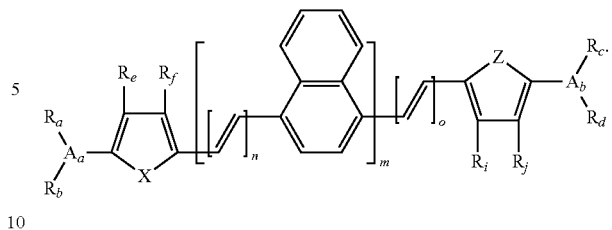
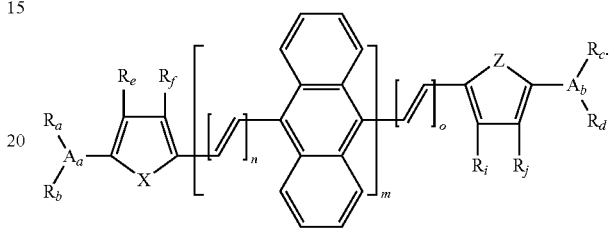
* * * * *